United States Patent [19]

Sartorius et al.

[11] Patent Number: 5,185,645
[45] Date of Patent: Feb. 9, 1993

[54] MEASUREMENT METHOD FOR THE DETERMINATION OF LOW LEVELS OF OPTICAL ABSORPTION

[75] Inventors: Bernd Sartorius, Berlin, Fed. Rep. of Germany; Alain Reboux; Bertrand Huet

[73] Assignee: Heinrich-Hertz-Institut für Nachrichtentechnik Berlin GmbH, Berlin, Fed. Rep. of Germany

[21] Appl. No.: 659,008

[22] Filed: Feb. 21, 1991

[30] Foreign Application Priority Data

Feb. 22, 1990 [DE] Fed. Rep. of Germany ....... 4005864

[51] Int. Cl.$^5$ ............................................. G01N 21/00
[52] U.S. Cl. .................................... 356/435; 356/432; 356/437
[58] Field of Search .................. 356/432–444, 356/380, 381, 382, 408–411, 414, 415, 320, 39, 41, 317, 318, 325; 250/573, 574, 575

[56] References Cited

U.S. PATENT DOCUMENTS

| | | | |
|---|---|---|---|
| 3,332,313 | 7/1967 | Batson | 356/408 |
| 3,910,701 | 10/1975 | Henderson et al. | 356/39 |
| 4,092,069 | 5/1978 | Fukuda et al. | 356/434 |
| 4,403,861 | 9/1983 | Boisde et al. | 356/419 |
| 4,704,576 | 11/1987 | Tributsch et al. | 324/158 R |
| 5,015,099 | 5/1991 | Nagai et al. | 356/437 |

OTHER PUBLICATIONS

M. R. Brozel, et al.; "Direct observation of the principal deep level (EL2) in undoped semi-insulating GaAs"; Apr. 1, 1983; Appl. Phys. Lett. 42(7); 610–612.

P. Dobrilla & J. S. Blakemore; Experimental requirements for quantitative mapping of midgap flaw concentration in semi-insulating GaAs wafers by measurement of near-infrared transmittance; Jul. 1, 1985; J. Appl. Phys. 58(1); 208–218.

Yoshinori Nakano & Nobuyori Tsuzuki; Active layer thickness measurement system for double heterostructure laser wafers; Jan. 1989; Optical Engineering vol. 28 No. 1; 042–045.

Transmissions-Photometer brochure from Pier-Electronic.

Primary Examiner—Richard A. Rosenberger
Assistant Examiner—Hoa Q. Pham
Attorney, Agent, or Firm—Nils H. Ljungman and Associates

[57] ABSTRACT

A measurement method is presented for the determination of low levels of optical absorption in any material, with at least a quasi-simultaneous detection of the transmission intensities of a measurement light beam and a reference light beam, the wavelengths of which are different, such that, essentially, the measurement light is absorbed by the material to be tested, and with a joint analog acquisition of the detected measurement and reference signals, taking into consideration the natural difference in intensities between the measurement light beam and the reference light beam.

40 Claims, 5 Drawing Sheets

MEASUREMENT METHOD FOR THE DETERMINATION OF LOW LEVELS OF OPTICAL ABSORPTION

FIELD OF THE INVENTION

The present invention relates to a measurement method for the determination of low levels of optical absorption in any material, with at least a quasi-simultaneous detection of the transmission intensities of a measurement light beam and a reference light beam, the wavelengths of which are different, such that, essentially, the measurement light beam is absorbed by the material to be tested, and with a joint analog acquisition of the detected measurement and reference signals, taking into consideration the natural difference in intensities between the measurement light beam and the reference light beam.

The use of a measurement light beam and a reference light beam with different wavelengths makes it possible to eliminate interfering effects, which may cause a systematic error in the measurement result. For this purpose, the wavelength of the measurement light beam is selected so that it is optimally absorbed by the material to be tested. Optimal absorption occurs with solids, liquids and gases, in a range of characteristic absorption bands, and in solids, above the band edge. The absorption capability of a material is therefore very closely dependent on the wavelength of the transmitting light beam. In addition, the measurement light beam is attenuated during transmission through the material to be tested by interfering factors such as reflection, scattering, dirt, etc., or by additional absorption by other media. Such interferences, as general losses, usually have a broad base, because they are only weakly dependent on the wavelength. The wavelength of the reference light beam is selected such that it is close to the measurement wavelength, but additionally such that it is in the transparent spectral range of the material to be tested. Therefore, the reference light beam is absorbed very little, but is essentially attenuated only by the interference. By means of the reference light beam, therefore, the transmission intensity is determined without absorption, but by means of the measurement light beam, the transmission intensity is determined with absorption. For the joint acquisition of the detected measurement and reference signals, the relative intensity attenuation by interference is largely identical in both light beams. If the signals are then balanced with regard to the natural intensity difference between the two wavelengths, the only intensity difference remaining corresponds physically to the optical absorption of the material to be tested.

BACKGROUND INFORMATION

A measurement process similar to the type described above is discussed in a brochure entitled "Transmissions-Photometer", published by Pier-Electronic GmbH, Nassaustrasse 35, D-6238 Hofheim-Wallau (Germany). By means of the process described therein, low levels of optical absorption are measured by a joint analog acquisition of measurement and reference signals detected in alternation at a high frequency of alternation, in the form of their quotient. The consideration of the natural intensity difference between the measurement light beam and the reference light beam is accomplished by the mathematical inclusion of an intensity quotient of the two light beams without any absorption by the material to be tested. The optical absorptions are therefore determined indirectly by this process, since the quotient determined is not a direct measurement of the optical absorption. The optical absorption is calculated only from the difference between the number 1 and the quotient. However, this conversion includes the possibility of increased error propagation. With low levels of absorption, in particular, relatively severe changes in the optical absorption (e.g., from 1% to 2%; i.e., by a relative 100%) result in only small changes in the quotient (e.g., from 0.99 to 0.98; i.e., by a relative 1%). Even small measurement errors, or rounding off for digitization, thus cause a much greater inaccuracy in the determination of the optical absorption. With low levels of optical absorption in particular, the error can therefore automatically approach or exceed the order of magnitude of the absorption being measured.

OBJECT OF THE INVENTION

As the technology is refined, for many applications of the measurement process described, it becomes increasingly important to measure even low levels of optical absorption with high precision. It also becomes important to be able to measure the light absorption very rapidly. Moreover, the execution of a measurement process and the equipment required should always be simple and thus economical.

SUMMARY OF THE INVENTION

A measurement process carried out according to the present invention meets these high requirements, in that low levels of optical absorption can be measured directly by the joint acquisition of the detected measurement and reference signals in the form of a subtraction, with an automatic consideration of the natural intensity difference between the measurement and reference light beams being accomplished by a tuning of the difference formed to zero, during a preliminary measurement carried out in the absence of the material to be tested.

On account of the direct measurement of the levels of optical absorption, the measurement process according to the invention is very precise and rapid. The measurement can be called "direct", because the analog-formed difference between the measurement and reference signal reflects the physical definition of the absorption. As a result of the automatic consideration of the natural intensity difference, therefore, and without any additional computational effort or time, the desired measurement of optical absorption is directly achieved. The high measurement speed thereby achieved is accompanied by a high measurement resolution, since the resolution range comprises only the order of magnitude of the difference, and not the order of magnitude of the individual values, which may be several times greater. A significant improvement of the measurement accuracy is achieved by the measurement process according to the invention, in that the mechanical error included in the direct subtraction is not increased. In other words, the absolute measurement error is also reduced for low levels of optical absorption, but the decisive relative error remains almost unchanged. The influence of interfering factors which are only weakly dependent on the wavelength is also reduced by the subtraction, so that it becomes substantially insignificant. Fluctuations of the light sources and of the evaluation electronics over time are completely compensated with the type of direct subtraction utilized according to the invention.

The article entitled "Direct Observation of the Principal Deep Level (EL2) in Undoped Semi-insulating GaAs", Brozel et al., Appl. Phys. Lett. 42(7), Apr. 1, 1983, pages 610 ff., discusses the formation of a difference from the detected measurement and reference signals. However, the difference proposed therein is calculated mathematically. For that purpose, the measurement and reference signals are individually and digitally acquired, but at different times. The relative error which occurs relates to the large individual values measured. It is therefore decisively greater than the relative error, which is made during the direct measurement of the significantly smaller difference. Erratic errors can also occur during the digitization. The measurement and reference signals are also detected at significantly different times, so that, for results which are in any way accurate, the measurement and reference light beams and the electronic system used for their evaluation must be very stable over time. The measurement results are available only after all the individual signals have been acquired and processed by computer.

A direct measurement of the optical absorption or the intensity difference by means of a joint analog acquisition of the detected measurement and reference signals is discussed in "Experimental Requirements for Quantitative Mapping of Midgap Flaw Concentration in Semi-Insulating GaAs Wafers by Measurement of Near-Infrared Transmittance", Dobrilla et al., J. Appl. Phys. 58(1), Jul. 1, 1985, pages 208 ff. In a measurement method discussed therein, the light absorption is first precisely determined, at great effort, at one reference point on the material to be tested, and is electronically compensated. In the subsequent measurements, the relative light absorption is directly measured as the difference from the absorption at the reference point. The measurement and reference light beams discussed in this article, however, have the same wavelength. Reflection losses as systematic errors are therefore taken into consideration mathematically, at the expense of a corresponding discrepancy from reality and a substantially large investment of time. Scattering losses are not taken into consideration. Since the detection of the measurement and reference light beams are done at times which are a considerable period apart, the measurement light beam, the compensation signal and the evaluation electronic system must be constructed to be correspondingly stable over time, resulting in substantially increased expense.

In spite of its high measurement precision and speed, the measurement method according to the present invention is simple to perform. This simplicity is due to the uncomplicated direct subtraction, and, in particular, to the automatic consideration of the natural intensity difference in the subtraction. The intensity difference must be taken into consideration to get a directly usable result in the difference formed, a result which is independent of the natural, different intensities of the measurement and reference light beams on account of their different wavelengths. In contrast to the mathematical consideration in the prior art, this consideration of the natural intensity difference between the two different wavelengths is done automatically in the process according to the invention. For that purpose, all that is necessary is to set (or "zero-tune") the measured difference to zero before the beginning of a measurement series, without the presence of the material to be tested. A knowledge of the individual parameters, by measurement or calculation, is not necessary for this purpose. This "zero-tuning" compensates for the natural intensity difference between the measurement and reference light beams, so that all the interference parameters have approximately the same influence. Only by means of this compensation, in which essentially all the interfering factors which occur are eliminated during the subtraction, except for a minor difference on account of their very slight dependence on wavelength, does the direct measurement of the difference or light absorption become at all possible and efficient. In addition, matrix effects caused by environmental factors can also be taken into consideration by means of the "zero tuning".

In one advantageous embodiment of the measurement process according to the invention, the tuning of the difference to zero can be optically performed by attenuating the intensity of the stronger of the two light beams. Such a process step is very simple and requires only an uncomplicated adjustment (e.g., of a grey filter) in the corresponding beam path. In this embodiment, the reproducibility of the grey setting is achieved, for example, by the adjustment of a micrometer screw.

In another embodiment of the invention, which is more elegant, but which accomplishes the same effect, the tuning of the difference to zero is performed electronically by setting a corresponding weighting in the subtraction. In this embodiment, the zero tuning can be performed very precisely (e.g., by a computer) by digitally changing amplification factors before the subtraction by means of a controllable resistance cascade. Such digital manipulation of acquired test results are well known in the prior art. The exact reproducibility and continuous control capability of the zero tuning are thus guaranteed. No mechanical adjustment problems and drift related thereto can occur. The zero tuning is therefore stable over time.

Both of the zero tuning methods described above are preferably performed directly in the measurement apparatus. That is, they are closely related to the measurement method itself, in contrast to, for example, a mathematical compensation by a specified characteristic, which would be solved by means of a process separate from the measurement method itself.

In another embodiment of the measurement method according to the invention, the measurement and reference light beams are each generated by a preferably separate monochromatic light source. Possible light sources include laser diodes, for example. On account of their low beam diameter, these diodes ensure a high spot resolution. By means of an appropriate optical configuration, the two light means can be sent to the material to be tested in a single beam path, at rapidly alternating intervals. The measurement and reference light beams can be either alternated mechanically by a chopper blade, for example, or electrically by a modulation of the laser diodes. In the former case, one light beam is always covered; in the latter case, the two laser diodes are activated in alternation. In both cases, a computer control preferably can be used.

The article entitled "Active Layer Thickness Measurement System for Double Heterostructure Laser Wafers", Nakano et al., OPTICAL ENGINEERING, January 1989, Volume 28, No. 1, Pages 042 ff., discusses the use of two laser diodes for the determination of net absorption in laser structures. However, these are operated one after the other at a very great interval, i.e., the material to be tested is first scanned completely with the measurement light beam and then with the reference light beam. This requires more time for the individual measurements, and makes the measurement process correspondingly longer. A very good stabilization of the laser diodes to avoid power or temperature drift is therefore necessary. In the measurement process discussed in this article, there is no power equalization of the two laser diodes. The power ratio of the two laser diodes without absorption is calculated. The measurement results are determined by a computer and are available, as a quotient, only after the completion of the second scanning process. In addition to the above-mentioned large error factor in the determination of low levels of optical absorption by forming a ratio from individual values, on account of the great time between the two measurement passes with two different scans of the material to be tested, there are also calibration problems in achieving identical measurement points.

In another embodiment of the measurement process according to the invention, it is advantageous if the measurement and reference light beams are filtered from a light beam generated by a single light source which is optically split after transmission through the material being tested. This process step guarantees that the measurement and reference light beam pass through the material to be tested in exactly the same beam path. The measurement point is thus defined with precision and is identical for both beams. Complex calibrations for beam overlapping at the measurement point and in the remainder of the beam path, displacement of the material to be tested and optical beam deflectors are, as a result of the invention, avoided. Fluctuations of the intensity of the light source itself have corresponding effects on the measurement and reference light beams, so that these fluctuations are compensated in the subtraction by automatic consideration of the natural intensity difference. According to one particular embodiment of the invention, the light beam is optically divided only after the material transmission, so that the measurement light beam and the reference light beam can be filtered out of the two separate light beams which are formed by the optical division. For the optical separation, it is thus relatively insignificant in what ratio the light beam is divided, since this is automatically taken into consideration in the subtraction by the above-mentioned zero tuning, with an unchanged splitting ratio by the resulting balancing of the two light beams. The precision of the determination of the light absorption as a percentage is not thereby affected. It is not really even of any interest to know the splitting ratio, which can be anything at all, so that extremely simple (and, therefore, inexpensive) components can be used to perform the splitting.

If, according to another advantageous embodiment of the process according to the invention, the measurement and reference light beams are cycled (or "modulated" or flashed) in alternation in a first frequency and the reference light beam is cycled in a second frequency, lock-in amplification technology, well known in the prior art, can be used for the analog measurement of the measurement and reference signals. This makes it possible to differentiate the signals detected on the basis of the frequencies artificially imprinted on them. Such a process step is always appropriate if the measurement and reference signals are generated by a single detector. Thus, with the use of two frequencies according to this embodiment of the invention, it becomes possible, on the one hand, to acquire both the measurement and reference signals for the subtraction, and, on the other hand, for example, only the reference signals for standardization purposes. Additional interfering factors, in particular general background interference, such as room light or dust in the beam path, can be eliminated by means of the lock-in amplification technology. The only signals which are processed are those which have previously been assigned specified frequencies and also phases. Interferences with other frequencies and other phases are not taken into consideration.

If the measurement and reference light beams are filtered out of a single light beam, in an additional advantageous embodiment of the invention, it is appropriate to cycle the joint beam of light. Lock-in amplification technology, with its known advantages, can once again be used for this purpose. Since only one frequency is used, the time constant of the lock-in amplifier can be selected to be very small, which leads to a higher measurement speed. To differentiate the measurement and reference signals for the subtraction and for standardization purposes, two detectors are used for this purpose, the two detectors preferably utilizing simple electronic components.

Lock-in amplification technology is, as noted above, well known in the art and is described, for example, in the publication entitled "Model 5210 Lock-in Amplifier Instruction Manual" (4200-0325, 19874-A-MNL), published by EG&G, Princeton Applied Research.

Another advantageous and very important refinement of the measurement process according to the invention specifies that the detection of the transmission intensities is done simultaneously by the measurement and reference light beam. As a result of this step, from the quasi-simultaneity of the detection method of the prior art to genuine simultaneity, the time-dependent interfering factors, such as characteristic and temperature drift of the light sources, the detectors or the evaluation unit are first eliminated. In addition, however, in the present invention the measurement speed can be increased, since the signal no longer needs to be buffered until an additional signal is received. Therefore, the errors connected with the buffering are also eliminated. With the elimination of the buffering as a result of simultaneous detection, it also becomes possible to form one or more continuous measurement series from the analog measurements. The discretization of the measurements for purposes of buffering is eliminated. According to this configuration of the invention, the material to be tested can therefore be tested continuously, e.g., in a continuous flow or over a given area, for its absorption behavior, which can change extremely rapidly. A prerequisite for simultaneous detection is that the measurement light beam and the reference light beam, after traversing the material to be tested, are present simultaneously, so that they can be conducted simultaneously to two detectors. This prerequisite is fulfilled by the configuration of the invention described above, in a simple manner, in that the measurement and reference light beams are filtered from a single light beam after it has been split.

In another refinement of the measurement method according to the invention, the low levels of optical absorption are measured as a function of position. The measured absorption can thereby be assigned to a specified location. Such a method is particularly advantageous if there are non-uniformities, as is frequently the case with solid objects. By varying the location, the absorption can then be determined discretely or continuously, according to the selection of the appropriate process stepwise over the entire surface of the solid body of test material.

In another configuration, and with location-specific measurement, it is also advantageous if the measurement and reference light beams are focused on the measurement point. The measurement point itself thereby becomes very small, which results in an increase in the spot resolution.

In general, the focus and/or the measurement point for the determination of absorption in a solid body are on its top side on the layer to be measured, and wherein the solid body upon which the layer is formed is disposed between the layer and the light source, to guarantee a high resolution. Scattering on its back side can be detected with a standard convergent lens, if the back side can be considered relatively smooth. However, if the solid body to be tested has a rough back side, in an additional configuration of the process according to the invention, it is advantageous if the focus is on the body's back side. Thus the absorption by the solid body can be precisely determined, without scattering of the light beam on the rough back side leading to distortions. The scattering which also occurs on extremely rough surfaces is then preferably in the focus of a downstream convergent lens, the aperture of which is preferably selected so that it is large enough to almost completely detect the scattered light in comparison to the illumination cone.

In another embodiment of the measurement method according to the invention, it is advantageous, when the material to be tested is provided with a reflecting back side, if the detection of the transmission intensities is performed on the incident side. By means of this step, the measurement method can also be used for a continuous process monitoring in fluids or gases, or for solids where the transmission of the measurement and reference light beams through their back side is impossible or difficult to achieve. A prerequisite is that the measurement and reference light beams are reflected from the back side of the material to be tested or, if the material does not sufficiently reflect the light, from an additional mirror connected to the back side. This prerequisite applies for observation chambers for process sequences in liquid or gaseous media with a mirror on the back wall of the chamber or, in particular, for solid body test pieces with metal contacts or on metal supports. In this method, it is also advantageous that the measurement apparatus takes up relatively little space. This configuration of the measurement method according to the invention is therefore particularly well-suited for test pieces in cryostatic temperature regulators, preparation chambers, etc. The same is true for test pieces which are accessible only from one side. With this process step, the double absorption which takes place must also be taken into account. Moreover, the reference signal must be corrected by a percentage which is already reflected on the test piece surface, and thus does not contribute to the absorption.

If the percentage of light reflected on the surface of the material to be tested is unknown, or if it changes, then it cannot be taken into consideration mathematically. It is then advantageous, according to an additional configuration of the invention, if the material to be tested is, provided with an opaque reflecting back surface and is illuminated according to the method well known in the prior art as the "dark field" principle. In this process, which is, as mentioned, well known in the prior art, the percentage of light reflected on the surface of the test piece which is not contributing to absorption, is geometrically blocked out of the detection beam path. The percentage of light guided to the absorption, on the other hand, is scattered over such a large angle that it gets past the blocking apparatus and can be detected. The "dark field" principle is described in LEXICON DER OPTIK, Herausgegeben von Heinz Helerkorn, VEB Bibliographisches Institut Leipzig (1988).

In another refinement of the measurement method according to the invention, the measurement method is combined with the well known luminescence measurement method for the determination of characteristic properties of the material to be tested. This luminescence measurement process, well known in the prior art, operates with a short-wavelength laser to excite luminescence, a dichroic mirror, which reflects or transmits the radiation as a function of the wavelength of the radiation, and a monochromator with a downstream detector to pick up the long-wavelength emission spectra. Characteristic properties of the material to be tested can be determined by means of its luminescence, in particular the characteristics of semiconductors, and in particular the band edge. As a result of the combination of the two measurement processes, which can be done optically, for example, by means of a switchable tilted mirror, the necessary characteristic properties and then the low levels of optical absorption can be determined for the material to be tested in a single preparation and apparatus. The combination of the two methods results in a major saving of time and effort, and places a reduced load on the material to be tested. In expensive clean rooms, the space saved by a combination of the two process arrangements is of extreme importance.

There are many possible uses for the measurement process according to the invention for the determination of low levels of optical absorption. A particular advantage of the process disclosed herein is that it operates non-destructively and without any adverse effect on the material to be tested. Moreover, the absorption measurements can be performed on solid, liquid and gaseous materials. Still further, the measurements can be conducted discretely or continuously, without regard to location for flowing materials or with a high spot resolution for solid bodies.

The light absorption values measured can be used for various determinations. To be able to explain these possible uses in greater detail, it is helpful to consider the mathematical formula used to calculate the light absorption:

$$I = I_0 \cdot e^{-kd} = I_0 \times e^{-at}$$

where:
I = Light intensity with absorption;
$I_o$ = Light intensity without absorption;
$k\alpha$ = Absorption coefficient; and
dt = Material thickness;

For small values of kd, the factor $e^{-kd}$ can be replaced by its Taylor series:

$$e_\eta^{-kd} = 1 - kd + (kd)^2/2 - (kd)^3/6 + \ldots$$

Since the exponents for a small kd become extremely small, the following can be used as a good approximation:

$$e_\eta^{-kd} \simeq 1 - kd$$

This gives, for I:

$$I = I_o*(1-kd)$$

and/or $$(I_o - I)/I_o = kd = \alpha t$$

whereby the difference $I_o - I$ is the light absorption which can be measured directly with the measurement method according to the invention.

If, by using the measurement method according to the invention, there is known the light absorption $I_o - I$ and $I_o$ as the intensity of the reference light beam without absorption, then according to the formula set forth above, the absorption coefficient of the material to be tested can be determined, if its thickness is known. Conversely, the thickness can be determined if the absorption coefficient is known. For sandwich test pieces, the thicknesses of the different layers can be determined selectively, if they have different band edges and thus different absorption characteristics. A third possibility is that, with a known thickness and a known absorption coefficient of the material to be tested, it becomes possible to perform concentration measurements of the species responsible for the absorption, e.g., dopants or impurities in solids or foreign media or particles in liquids or gases. Analyses of biological or chemical preparations are also possible.

The measurement method according to the invention is of particular interest for the determination of low levels of optical absorption for the measurement of layer thicknesses in semiconductor materials. By means of modern technologies for the manufacture and processing of such semiconductor layers, the layers are becoming thinner and thinner, but also increasingly susceptible. Therefore, it has become necessary to be able to control with great precision the composition and thickness of semiconductor layers, which can be a mere 1 nm in thickness, for example, in an extreme case. Deviations in the thickness, undesirable structural defects or a poor distribution of dopants can make the semiconductor unusable. This is particularly true for use with the so-called "Quantum-Well Lasers". With such lasers, the wavelengths can be adjusted and the threshold current minimized by the selection of the layer thickness, which is so extremely thin that the solid behavior of the material has already been modified. In addition, it is extremely important as part of the production process to be able to completely test each semiconductor chip. Random samples of parts or destructive tests are out of the question here. It is precisely for this application, among others, that the measurement process according to the invention is excellently suited. It can measure a range of layer thicknesses from approximately 0.01 to 2 micrometers. Moreover, it is nondestructive, extremely precise, very fast and makes continuous layer thickness measurements possible. The various embodiments described herein are, therefore, set forth primarily in the context of this type of application.

One aspect of the invention resides broadly in a measurement method for determining the optical absorption of a test material comprising the steps of: a) providing a light source for generating a light beam having a spectrum which includes at least a substantially monochromatic reference light beam (R) at a reference wavelength ($\lambda_R$) and a substantially monochromatic measurement light beam (M) at a measurement wavelength ($\lambda_M$); b) providing detector means for detecting the strength of the reference light beam (R) by generating a reference detector signal ($U_R$) when illuminated by the reference light beam (R) and for detecting the strength of the measurement light beam (M) by generating a measurement detector signal ($U_M$) when illuminated by the measurement light beam (M), each of the reference and measurement detector signals ($U_R$ and $U_M$) generated by the detector means being a signal indicative of the intensity of illumination of the detector means by the reference and measurement light beams (R and M), respectively; c) providing difference registration means for registering a difference between the reference detector signal ($U_R$) and the measurement detector signal ($U_M$) generated by the detector means when illuminated by the reference light beam (R) and the measurement light beam (M), respectively; d) directly illuminating the detector means with the reference light beam (R) to produce a first reference detector signal ($U_{Ra}$), the direct illumination of the detector means by the reference light beam (R) being carried out with the test material absent from the path of the reference light beam (R); e) directly illuminating the detector means with the measurement light beam (M) to produce a first measurement detector signal ($U_{Ma}$), the direct illumination of the detector means by the measurement light beam (M) being carried out with the test material absent from the path of the measurement light beam (M); f) registering a difference ($\Delta = U_{Ra} - U_{Ma}$) between the first reference detector signal ($U_{Ra}$) generated by the detector means when directly illuminated by the inference light beam (R) and a first measurement detector signal ($U_{Ma}$) generated by the detector means when directly illuminated by the measurement light beam (M); g) providing attenuation means for tuning to zero the difference ($\Delta$) between the first reference detector signal ($U_{Ra}$) and the first measurement detector signal ($U_{Ma}$) by attenuating one of the first reference detector signal ($U_{Ra}$) and the first measurement detector signal ($U_{Ma}$); h) actuating the attenuation means to thereby balance the first reference detector signal ($U_{Ra}$) and the first measurement detector signal ($U_{Ma}$) to identical values ($U_{Rb} = U_{Mb}$) and thereby tuning to zero the difference ($\Delta$) and maintaining this actuated balanced attenuation status during the following steps: i) passing the reference light beam (R) through the test material and thereafter illuminating the detector means with the reference light beam (R) to thereby generate a second reference detector signal ($U_{Rc}$); j) passing the measurement light beam (M) through the test material and thereafter illuminating the detector means with the measurement light beam (M) to thereby generate a second measurement detector signal ($U_{Mc}$); and k) measuring the difference ($\Delta I$) between the second reference signal ($U_{Rc}$) and the second measurement signal ($U_{Mc}$); whereby the difference ($\Delta I$) is directly indicative of the optical absorption (LA) of the test material.

Another aspect of the invention resides broadly in a measurement method for determining the optical absorption of a semiconductor layer or a semiconductor wafer, the measurement method comprising the steps of: a) providing a light source for generating a light beam having a spectrum which includes at least a substantially monochromatic reference light beam (R) at a reference wavelength ($\lambda_R$) and a substantially monochromatic measurement light beam (M) at a measurement wavelength ($\lambda_M$); b) providing detector means for detecting the strength of the reference light beam (R) by generating a reference detector signal ($U_R$) when illuminated by the reference light beam (R) and for detecting the strength of the measurement light beam (M) by generating a measurement detector signal ($U_M$) when illuminated by the measurement light beam (M), each of the reference and measurement detector signals ($U_R$ and $U_M$) generated by the detector means being a signal indicative of the intensity of illumination of the detector means by the reference and measurement light beams (R and M), respectively; c) providing difference registration means for registering a difference between the reference detector signal ($U_R$) and the measurement detector signal ($U_M$) generated by the detector means when illuminated by the reference light beam (R) and the measurement light beam (M), respectively; d) directly illuminating the detector means with the reference light beam (R) to produce a first reference detector signal ($U_{Ra}$), the direct illumination of the detector means by the reference light beam (R) being carried out with the semiconductor layer or semiconductor wafer absent from the path of the reference light beam (R); e) directly illuminating the detector means with the measurement light beam (M) to produce a first measurement detector signal ($U_{Ma}$), the direct illumination of the detector means by the measurement light beam (M) being carried out with the semiconductor layer or semiconductor wafer absent from the path of the measurement light beam (M); f) registering a difference ($\Delta = U_{Ra} - U_{Ma}$) between the first reference detector signal ($U_{Ra}$) generated by the detector means when directly illuminated by the inference light beam (R) and a first measurement detector signal ($U_{Ma}$) generated by the detector means when directly illuminated by the measurement light beam (M); g) providing attenuation means for tuning to zero the difference ($\Delta$) between the first reference detector signal ($U_{Ra}$) and the first measurement detector signal ($U_{Ma}$) by attenuating one of the first reference detector signal ($U_{Ra}$) and the first measurement detector signal ($U_{Ma}$); h) actuating the attenuation means to thereby balance the first reference detector signal ($U_{Ra}$) and the first measurement detector signal ($U_{Ma}$) to identical values ($U_{Rb} = U_{Mb}$) and thereby tuning to zero the difference ($\Delta$) and maintaining this actuated balanced attenuation status during the following steps: i) passing the reference light beam (R) through the semiconductor layer or semiconductor wafer and thereafter illuminating the detector means with the reference light beam (R) to thereby generate a second reference detector signal ($U_{Rc}$); j) passing the measurement light beam (M) through the semiconductor layer or semiconductor wafer and thereafter illuminating the detector means with the measurement light beam (M) to thereby generate a second measurement detector signal ($U_{Mc}$); and k) measuring the difference ($\Delta I$) between the second reference signal ($U_{Rc}$) and the second measurement signal ($U_{Mc}$); whereby the difference ($\Delta I$) is directly indicative of the optical absorption (LA) of the semiconductor layer or semiconductor wafer.

Yet another aspect of the invention resides in an optical absorption measurement apparatus for determining the optical absorption of a test material, the optical absorption measurement apparatus comprising: a light source for generating a light beam having a spectrum which includes at least a substantially monochromatic reference light beam (R) at a reference wavelength ($\lambda_R$) and a substantially monochromatic measurement light beam (M) at a measurement wavelength ($\lambda_M$); b) detector means for detecting the strength of the reference light beam (R) by generating a reference detector signal ($U_R$) when illuminated by the reference light beam (R) and for detecting the strength of the measurement light beam (M) by generating a measurement detector signal ($U_M$) when illuminated by the measurement light beam (M), each of the reference and measurement detector signals ($U_R$ and $U_M$) generated by the detector means being a signal indicative of the intensity of illumination of the detector means by the reference and measurement light beams (R and M), respectively; c) difference registration means for registering a difference between the reference detector signal ($U_R$) and the measurement detector signal ($U_M$) generated by the detector means when illuminated by the reference light beam (R) and the measurement light beam (M), respectively; d) reference direct illumination means for directly illuminating the detector means with the reference light beam (R) to produce a first reference detector signal ($U_{Ra}$), the direct illumination of the detector means by the reference light beam (R) being carried out with the test material absent from the path of the reference light beam (R); e) measurement direct illumination means for directly illuminating the detector means with the measurement light beam (M) to produce a first measurement detector signal ($U_{Ma}$), the direct illumination of the detector means by the measurement light beam (M) being carried out with the test material absent from the path of the measurement light beam (M); f) registration means for registering a difference ($\Delta = U_{Ra} - U_{Ma}$) between the first reference detector signal ($U_{Ra}$) generated by the detector means when directly illuminated by the inference light beam (R) and a first measurement detector signal ($U_{Ma}$) generated by the detector means when directly illuminated by the measurement light beam (M); g) attenuation means for tuning to zero the difference ($\Delta$) between the first reference detector signal ($U_{Ra}$) and the first measurement detector signal ($U_{Ma}$) by attenuating one of the first reference detector signal ($U_{Ra}$) and the first measurement detector signal ($U_{Ma}$); h) means for actuating the attenuation means to thereby balance the first reference detector signal ($U_{Ra}$) and the first measurement detector signal ($U_{Ma}$) to identical values ($U_{Rb} = U_{Mb}$) and thereby tuning to zero the difference ($\Delta$) and maintaining this actuated balanced attenuation status regarding the means specified as follows: i) means for passing the reference light beam (R) through the test material and thereafter illuminating the detector means with the reference light beam (R) to thereby generate a second reference detector signal ($U_{Rc}$); j) means for passing the measurement light beam (M) through the test material and thereafter illuminating the detector means with the measurement light beam (M) to thereby generate a second measurement detector signal ($U_{Mc}$); and k) means for measuring the difference ($\Delta I$) between the second reference signal ($U_{Rc}$) and the second measurement signal ($U_{Mc}$); whereby the difference ($\Delta I$) is directly indicative of the optical absorption (LA) of the test material.

BRIEF DESCRIPTION OF THE DRAWINGS

The measurement method according to the invention and particularly preferred embodiments are explained in greater detail below and with reference to the accompanying drawings, the drawings being in the form of schematic diagrams, wherein.

DESCRIPTION OF THE PREFERRED EMBODIMENTS

Figure 1:
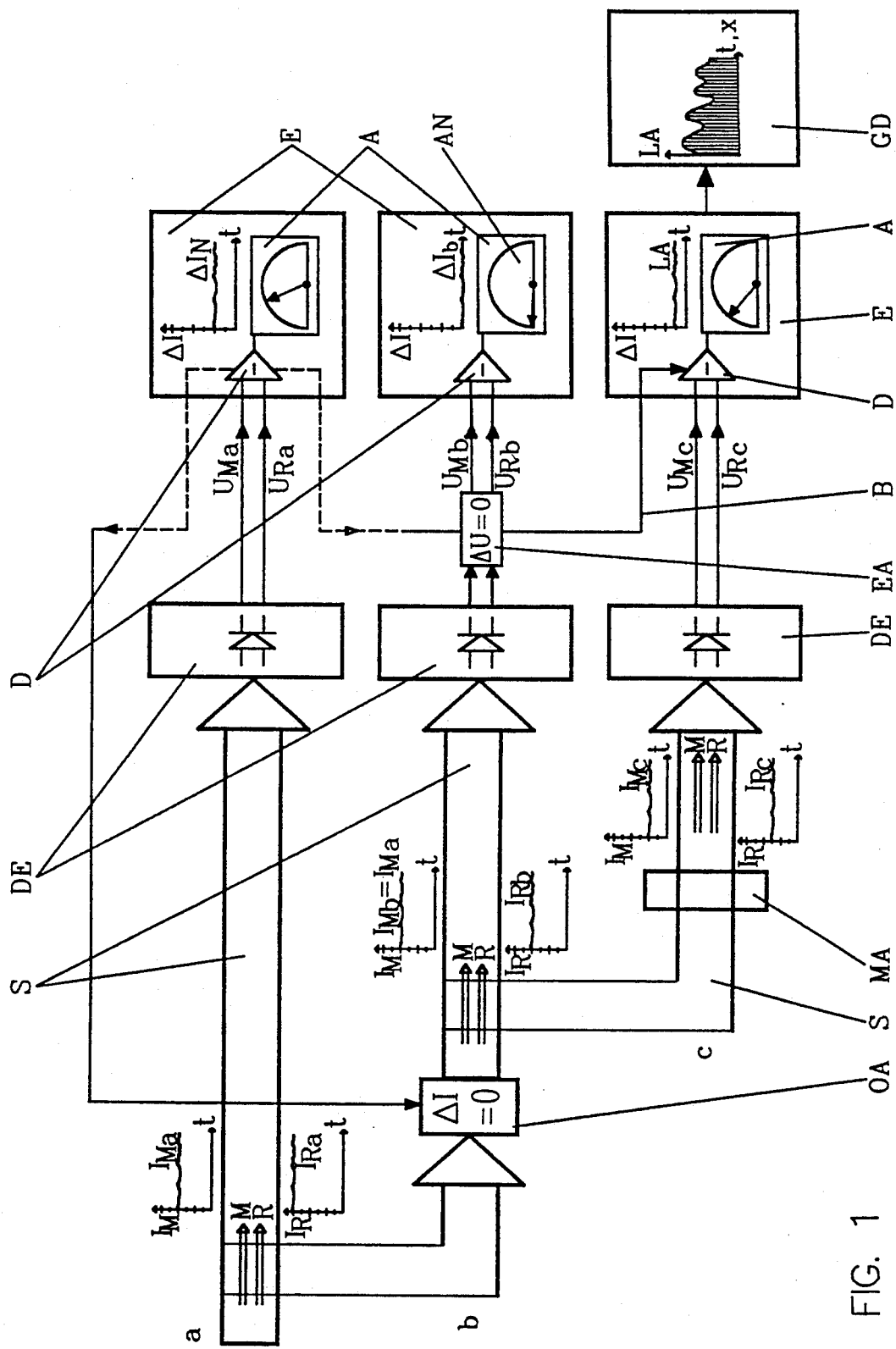
FIG. 1 is a schematic diagram illustrating the theoretical process according to the invention, in three stages.

Referring first to FIG. 1, a sequence presented schematically therein of the measurement process according to the invention for the measurement of low levels of optical absorption is divided into three process stages, designated a, b and c. In a Preliminary Stage a, a base measurement without the presence of the material MA to be tested is performed, to determine the current status of the measurement apparatus. In a Tuning Stage b, a zero shift, also determined in the Preliminary Stage a, is then tuned. Finally, in the Actual Measurement Stage c, the measurement series itself is performed. For purposes of illustration, the three process stages a, b, and c are illustrated in sequence in FIG. 1. The intensities $I_M$ and $I_R$ which occur are plotted over the measurement time t, and are shown in the small diagrams in FIG. 1 intended to clarify the relationships.

To perform the base measurement in the Preliminary Stage a, a measurement light beam M with a selected measurement wavelength $\lambda_M$ and a base intensity $I_{Ma}$, which is a function of the generation source, and a reference light beam R, with a selected reference wavelength $\lambda_R$ and a base intensity $I_{Ra}$, which is also a function of the generation source, are conducted to a detection device DE. As a function of the type of generation source, the measurement and reference light beams M and R can be configured either as individual beams or jointly (e.g., as a single relatively broad band or "white" light source having significant spectral components at the $\lambda_R$ and $\lambda_M$ wavelengths). In FIG. 1, this single joint beam is indicated by the illustration of a beam path S, which includes the measurement and reference light beams M and R at least as parts thereof. The detection DE of the base intensities $I_{Ma}$ and $I_{Ra}$ can be performed, as discussed more fully below, either by using one detector quasi-simultaneously, with a rapidly alternating transmission of the measurement and reference light beams M and R, or exactly simultaneously by using two detectors with a simultaneous transmission of the light beams M and R as part of a broader spectrum "white" light beam.

The detection DE device generates a measurement signal $U_{Ma}$ and a reference signal $U_{Ra}$. These are conducted to a joint analog acquisition device E. The joint acquisition in device E is preferably provided in the form of a subtraction D device for performing a subtraction between the measurement signal $U_{Ma}$ and the reference signal $U_{Ra}$. The result of this subtraction D is an intensity difference $\Delta I$ between the intensities $I_{Ma}$ and $I_{Ra}$, which is preferably displayed on an analog display apparatus A. For the base measurement in the Preliminary Stage no light absorption LA can occur, since no absorbing material MA is placed in the beam path S. The indicated intensity difference $\Delta I$ is, therefore, a natural intensity difference $\Delta I_N$ between the measurement and reference light beams M and R, which is due to the different wavelengths of the light beams, $\lambda_M$ and $\lambda_R$, and which leads to a different weighting of the measurement and reference light beams M and R. If this difference $\Delta I_N$ were not taken into consideration, it would falsify each measurement result, so that the values indicated on the analog display apparatus A would not allow a rapid and direct evaluation of the measured light absorption. Therefore, in the measurement method according to the invention, there is an automatic consideration B of the natural intensity difference $\Delta I_N$, in the form of a tuning AN of the difference $U_{M6}-U_{R8}$ to zero. There is therefore made possible-during the actual measurement stage-the interpretation each subsequent measurement result displayed on the analog display apparatus A without any additional compensation, in other words, as a directly measured light absorption LA of the tested material.

The tuning AN of the difference $U_{M8}-U_{R6}$ to zero takes place in a tuning measurement process step, represented schematically in FIG. 1 by the Tuning Stage b. Alternatively, either an optical zero tuning step OA or an electronic zero tuning step EA can be performed. Each alternative is indicated, in FIG. 1, by a showing of the possible lines of action in the subtraction D in the Preliminary Stage a in dashed form. However, preferably, only one of the two possible tunings is performed at any one time, both of which achieve substantially the same effect. When the optical zero tuning step OA is employed, the more intense of the two light beams M and R is attenuated until the difference $\Delta I_b$, indicated by the analog display apparatus A, becomes zero (I=O). Thus, in the example illustrated in FIG. 1, the base intensity $I_{Ra}$ of the reference light beam R is greater than the base intensity $I_{Ma}$ of the measurement light beam M. Therefore, the reference light beam R is attenuated (e.g., with a grey filter) until its tuned intensity $I_{Rb}$ is identical to the base intensity $I_{Ma}$ of the measurement light beam M, which is not affected. Thus, after the optical zero tuning step OA, $I_{Ma}=I_{Mb}=I_{Rb}$. By the optical zero tuning step OA, the measurement light mean M and the reference light beam R are optically balanced to one another, so that they now are subject to the same absolute attenuation by any external factors which are a function of the wavelength.

Substantially the same result can also be accomplished if the balancing is performed not optically but electronically, by means of an electronic zero tuning step EA. In this case, the intensities $I_{Ma}$ and $I_{Ra}$ remain unchanged, but their corresponding measurement and reference signals $U_{Ma}$ and $U_{Ra}$, respectively, are made to be electrically different by setting a corresponding weighting in the subtraction D, so that the signals $U_{Mb}$ and $U_{Rb}$ result, which difference between is then set to zero ($\Delta U=O$). The weighting can be preferably set, for example, by a computer-controlled modification of amplification factors during the subtraction D.

In addition to the tuning step AN to zero on account of the natural intensity difference $\Delta I_N$, matrix effects can also be compensated for with this same tuning step AN. For this purpose, in the Tuning Stage b, for example, a substrate layer (without an absorbing layer to be used later in the actual measurement step) which could distort the measurement, or a solvent (without the substance to be later analyzed) may be placed in the beam path S, and the resulting intensity difference ΔI may be then tuned to zero.

After the performance of the tuning measurement in the Tuning Stage b, using the optical tuning step OA or the electronic tuning step EA and, if necessary, a compensation for matrix effects, the natural intensity difference $\Delta I_N$ is always neutralized by automatically taking it into consideration B in terms of its influence on the measurement result. The measurement itself can now be performed in Measurement Stage c, also shown schematically in FIG. 1. For that purpose, the material MA to be tested is placed in the beam path S, so that the measurement light beam M and the reference light beam R are transmitted therethrough. The measurement beam, on account of its measurement wavelength $\lambda_M$, which would be selected above the absorption edge, or in the range of an absorption band of the material MA, is thereby optimally absorbed by the material MA. It is also attenuated as a result of additional interfering effects, in particular, as a result of reflection and scattering. Its base intensity $I_{Ma}$ is reduced to the transmission intensity $I_{Mc}$. The reference light beam R, on the other hand, has the reference wavelength $\lambda_R$, which is preferably selected in the transparent spectral range of the material MA to be tested near the measurement wavelength $\lambda_M$. Therefore, it is preferably only negligibly absorbed by the material MA, but is generally subject to the interfering effects which are present. Its tuning intensity $I_{Rb}$ for optical tuning OA ($I_{Ra}$ for electronic tuning EA) is reduced to the transmission intensity $I_{Rc}$, but in each case is still greater than the transmission intensity $I_{Mc}$ of the measurement light beam M. In the subsequent detection step DE, the measurement and reference light signals are detected as $U_{Mc}$ and $U_{Rc}$ (for optical tuning OA; $U_{Ma}$ and $U_{Ra}$ for electronic tuning EA, respectively). These signals are now transmitted to the analog subtraction device D, with an automatic consideration B of the natural intensity difference $\Delta I_N$. The rapid and precise result of the measurement of this subtraction D as a directly measured value is the light absorption LA by the material to be tested MA, all the interfering effects having been compensated for during the subtraction step D.

The measurement results of the light absorption LA can then be processed, e.g., in a graphic presentation device GD. The presentation can be made continuously or discretely as a function of the type of detection DE, either independent of a specific location over the entire measurement period t, or as a function of the measurement point x, depending on the type of material to be tested.

Figure 2:
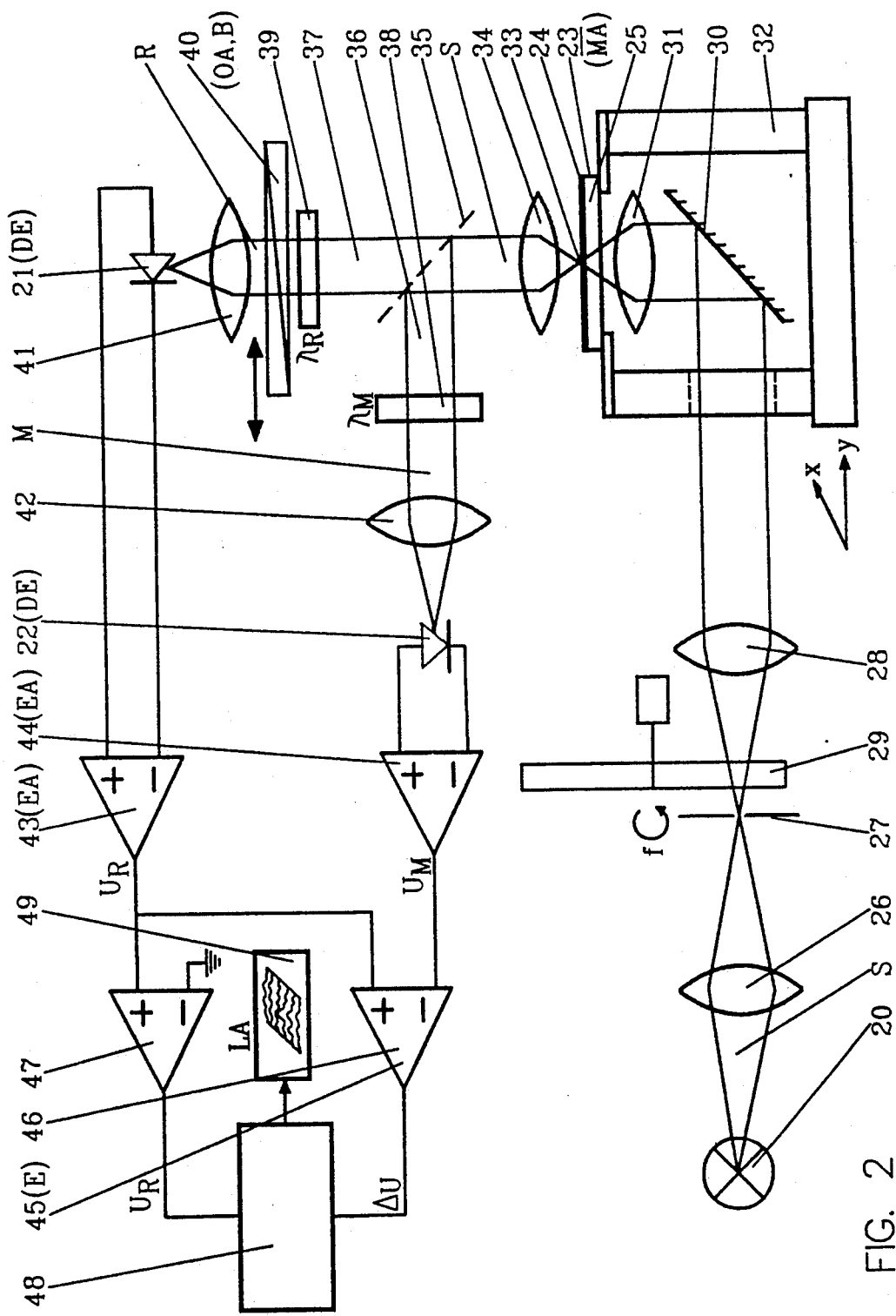
FIG. 2 is a schematic diagram of an apparatus for the performance of the measurement method according to the invention, with one light source and two detectors.

FIG. 2 is a schematic illustration of a first preferred embodiment for the performance of the measurement method according to the invention. This embodiment is characterized by the fact that a single light source 20 and two detectors 21 and 22 are employed. The detection step DE thus takes place exactly simultaneously. In the embodiment illustrated in FIG. 2, the material to be tested is a solid body, the thickness of which must be determined by measuring the light absorption LA. The solid body in question is preferably, for example, an epitaxial semiconductor chip 23 with an absorbing InGaAsP layer 24, which is epitaxially grown on a transparent InP substrate 25. The absorbing layer 24 is preferably between about 0.01 and about 2 micrometers thick, and the transparent substrate 25 is typically approximately 300 micrometers thick.

Starting from the light source 20, a common beam path S is first conducted through a first convergent lens 26, then through a space filter 27 and then through a second convergent lens 28, to improve the beam convergence. The space filter 27 (such "space filters" being well known in the art) acts as a fictitious light source and, with its strong diaphragm, is used to achieve an improved beam focusing for a highly-precise measurement point resolution. Behind the space filter 27 there is preferably provided a rotating chopper 29, which cycles the beam path S as flashing light, e.g., at a frequency f of, for example, 1 kHz. (The frequency f employed could be higher or lower, depending upon the technology available for implementation, such as for example, 100, 200, 300, 400, 500, 600, 700, 800, 900 Hz, 1.1, 1.2, 1.3, 1.4, 1.5, 1.6, 1.7, 1.8, 1.9, 2.0 kHz.) In this manner, and as will be explained in greater detail below, lock-in amplification technology can be used. Behind the second convergent lens 28, the beam path S strikes a tilted mirror 30, and from there it travels through a third convergent lens 31 and strikes the semiconductor chip 23, which is located on a measurement table 32 that can be preferably moved in at least two directions, x and y. On account of the smooth back side 25 of the semiconductor chip 23, a focusing point 33 is located on its upper side 24. If the solid body to be tested were to have a rough back side, the focusing point 33 would preferably be arranged to lie on this rough back side, so to be able to measure the scattered light as completely as possible. The diameter of the focusing point 33 is a function of the quality of the beam path S and, with good precision, can be on the order of 100 micrometers or less.

Disposed behind the semiconductor chip 23, there is provided a fourth convergent lens 34, for producing beam parallelism, which preferably has a large aperture corresponding to the scattering angle of the scattered light which occurs. Following this fourth convergent lens 34, the beam path S is conducted to a beam splitter 35, which divides the beam path S into two individual beams 36 and 37. On account of the zero tuning, the division ratio of the beam splitter 35 is irrelevant, because the division ratio is automatically taken into consideration. From the individual beam 36 deflected by the beam splitter 35, the measurement light beam M with the measurement wavelength $\lambda_M$ is filtered through by means of a measurement wavelength filter 38 (for example, a bandpass filter or arrangement of filters). This measurement wavelength $\lambda_M$ is preferably selected on the basis of the band edge of the absorbing InGaAsP layer 24 of the semiconductor chip 23, so that the measurement light beam M is maximally absorbed. During transmission, the measurement light beam M also experiences an attenuation as a result of interfering effects which occur, primarily reflection and scattering. The individual beam 37 which passes through the beam splitter 35 is conducted through a reference wavelength filter 39, whereby the reference light beam R with the reference wavelength $\lambda_R$ is selected and passed through the reference wavelength filter 39. The reference wavelength $\lambda_R$ is preferably selected in the transparent spectral range of the InGaAsP layer 24, in the vicinity of the band edge, so that the light absorption LA is only minimal. Therefore the reference light beam R is preferably attenuated only slightly during transmission by the semiconductor chip 23, primarily by the interfering effects.

In the illustrated embodiment, the natural intensity difference $\Delta I_N$ (See FIG. 1) between the measurement and reference light beams M and R is automatically equalized by the optical tuning step OA. For this purpose, there is provided a variable grey filter 40 disposed in the path of the reference light beam R. The position of this filter can be changed, either manually by means of a micrometer screw or, preferably, automatically by means of a computer control. After the artificial intensity attenuation by the grey filter 40, the reference light beam R is then conducted through a fifth convergent lens 41 to a first detector 21. The measurement light beam M passes without further external influence through a sixth convergent lens 42 and strikes a second detector 22. The simultaneous detection DE with the detectors 21 and 22 is made possible with the arrangement described above, because a single light beam S, containing the reference light beam R and the measurement light beam M as spectral components thereof, is optically divided after transmission through the material MA being tested, and the measurement and reference light beams M and R are thereafter filtered out of the individual beams 35 and 36 which are thereby produced, preferably by optical splitting. Each of the two detectors 21 and 22, which, in the example, are preferably InGaAs or Ge photodiodes, is connected to an electrical pre-amplifier 43 and 44, respectively, which convert the photocurrent produced by the detectors 21 and 22 into measurement and reference signals $U_M$ and $U_R$ in the form of voltages. By means of these preamplifiers 43 and 44, it is also possible to perform an electronic equalization by a computer-controlled variation of their amplification factors.

The measurement and reference signals $U_M$ and $U_R$ produced are then conducted to a joint analog acquisition E in the form of a difference amplifier 45, which, from the individual analog signals $U_M$ and $U_R$ forms the signal difference $\Delta U$ as an indicator of the desired light absorption LA. Since this signal difference $\Delta U$ is very small, it can be measured with high resolution precision. The difference amplifier 45 is preferably provided in the form of a first lock-in amplifier 46, by means of which it is possible to eliminate the frequency-selective and phase-selective interfering signals. Only the desired measurement and reference signals $U_M$ and $U_R$ are phase-selectively processed by this first lock-in amplifier 46, on account of its frequency of alternation f imposed by the chopper 29. By means of a preferably second lock-in amplifier 47, simultaneously with the analog-determined signal difference $\Delta_U$, the reference signal $U_R$ is measured. Both measurements $\Delta U$ and $U_R$ are necessary for the calculation of the layer thickness. This calculation is performed in the illustrated embodiment by means of a computer 48 (for example, one manufactured by Atari, Rhotron, etc.). The measurement table 32 and the variable grey filter 40 are also controlled by means of this computer 48, and the necessary calibration is performed. In the case of an electronic tuning EA, the computer 48 can also take over the control of the preamplification factors. The calculated layer thicknesses are then transmitted to a plotter 49, which is used in the example to create a three-dimensional layer thickness map of the semiconductor chip 23. In this embodiment, there is no separate, direct representation of the analog absorption values determined (GD, See FIG. 1).

Figure 3:
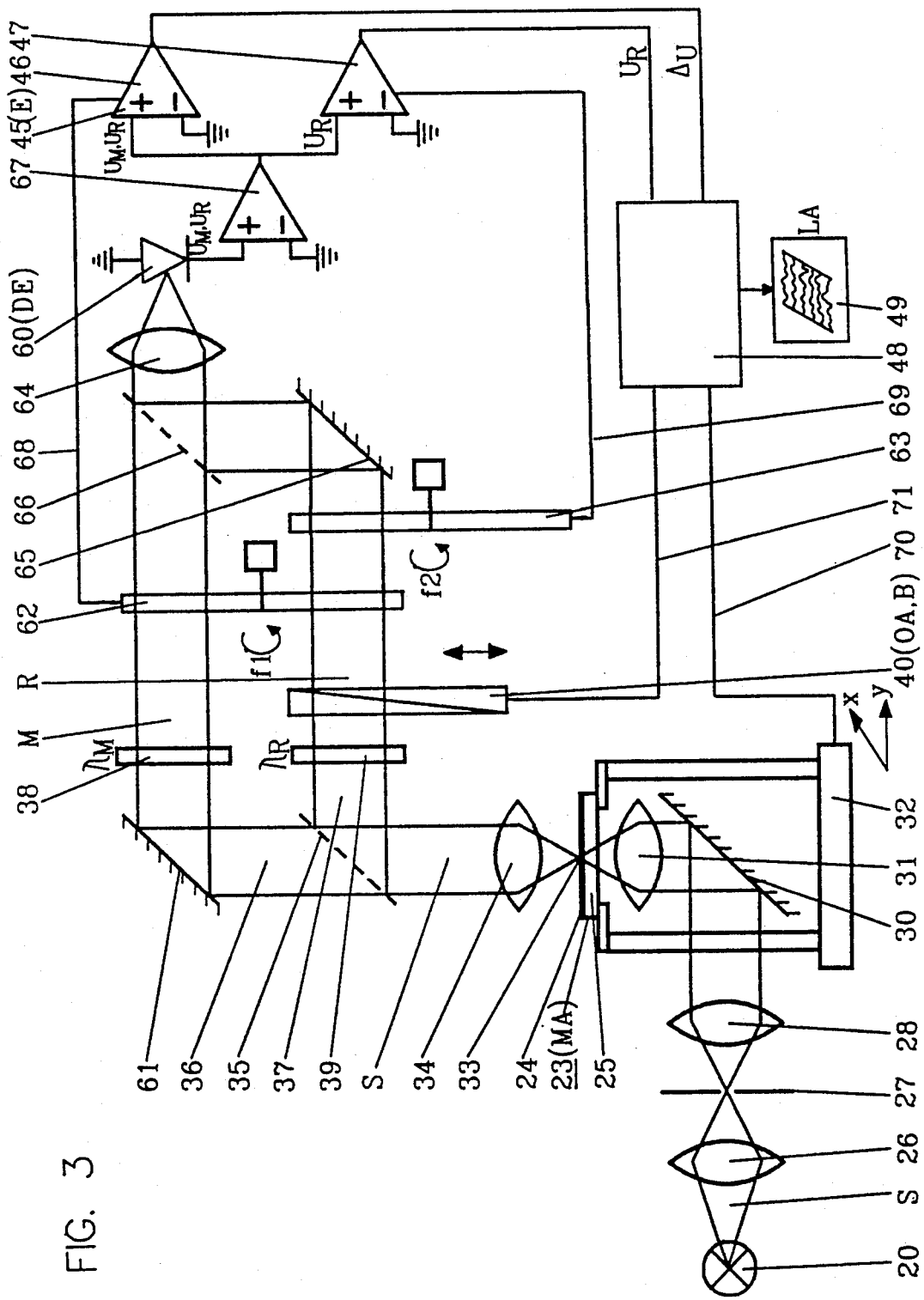
FIG. 3 is a schematic diagram of an apparatus for the performance of the measurement method according to the invention, with one light source and one detector.

FIG. 3 is a schematic illustration of an embodiment for the performance of the measurement method, which differs from the embodiment illustrated in FIG. 2 essentially in that only one detector 60 is used. The detection DE thus takes place quasi-simultaneously. In other words, as described more fully below, the term "quasi-simultaneously" as used herein, means that transmissions of the measurement light beam M and the reference light beam R, and the detections DE thereof, are performed in rapid successive alternation. The elements which are the same as in the optical configuration illustrated in FIG. 2 are identified by the same numbers, letters and symbols, and are not explained below in any further detail.

In the embodiment illustrated in FIG. 3, the first individual beam 36 is guided parallel to the second individual beam 37 by the provision of an additional tilted mirror 61. The measurement and reference light beams M and R are cycled (i.e., their transmission is rapidly alternated) by means of a first chopper 62 such that they alternate in a first frequency f1, and the reference light beam R is also further cycled by means of a second chopper 63 at a second frequency f2. The first cycling with the frequency f1 causes the measurement and reference light beams M and R to alternate in quick succession, and to be conducted by means of an additional convergent lens 64 to the single detector 60. For this purpose, an optical coupling of the reference light beam R into the beam path of the measurement light beam M is preferably accomplished, by means of a third tilted mirror 65 and a second beam splitter 66. By means of the coupling arrangement 65 and 66 described above, the reference light beam R is also transmitted at the frequency f2 set by the second chopper 63 to the detector 60. The single detector 60 therefore detects, in the first frequency f1, the measurement and light beams M and R in alternation and, in the second frequency f2, only the reference light beam R. The frequencies f1 and f2 may have magnitudes on the same order as frequency f, discussed above.

The measurement and reference signals $U_M$ and $U_R$ generated by the detector 60 are then conducted to preferably a single preamplifier 67. Since the signals $U_M$ and $U_R$ are processed only with the one detector 60 and the one preamplifier 67, any possible drift between several detectors and preamplifiers is avoided. The automatic consideration (B in FIG. 1) of the natural intensity difference $\Delta I_N$ is preferably performed exclusively by the optical tuning OA. On account of the different modulation, the difference $\Delta U$ is formed from the measurement and reference signals $U_M$ and $U_R$ by the first lock-in amplifier 46, whereby the first lock-in amplifier 46 is corrected by means of a line 68 which provides the frequency f1 of the first chopper 62. The reference signal $U_R$ is generated by the second lock-in amplifier 47, which is correlated by means of a line 69 with the frequency f2 of the second chopper 63. The computation and evaluation are performed by the computer 48. Additional control lines 70 and 71 are shown for providing computer generated automatic control of the measurement table 32 and of the variable grey filter 40 for performing the optical tuning step OA.

Figure 4:
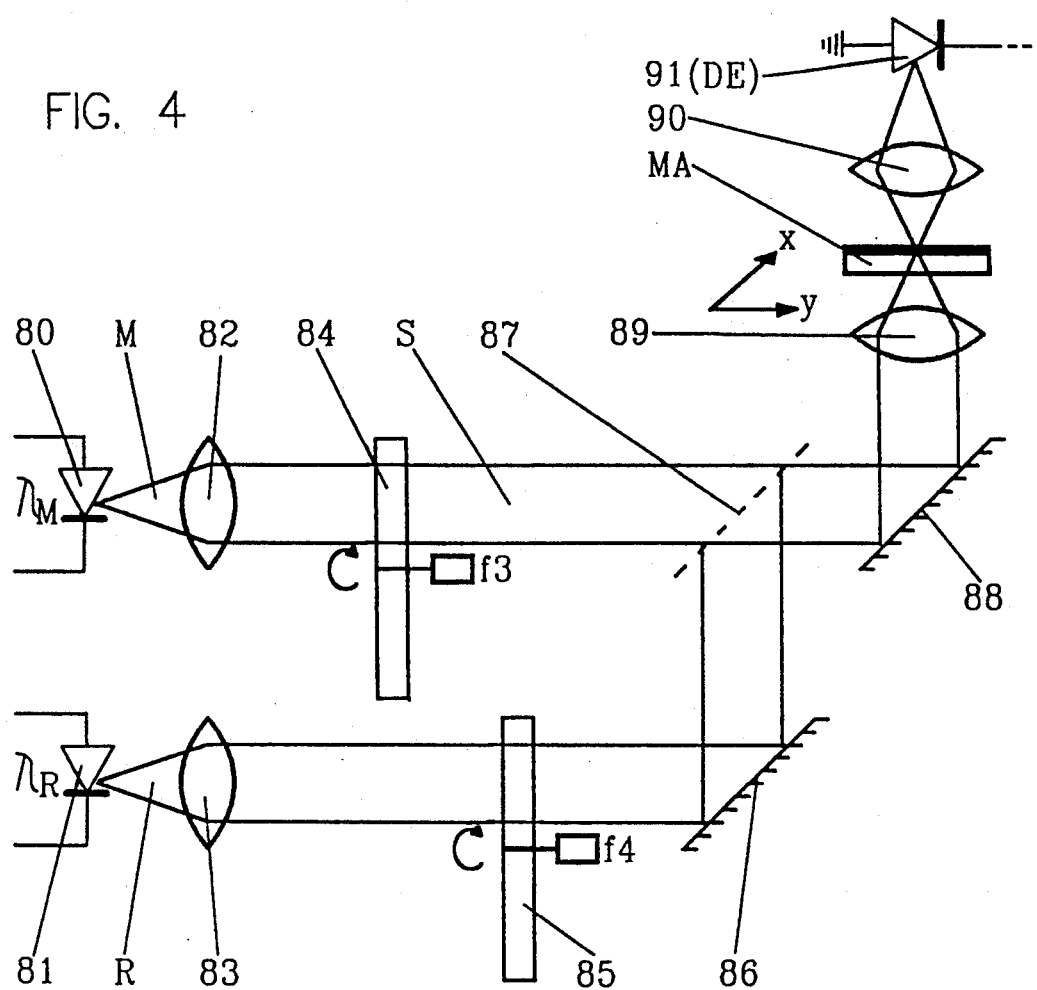
FIG. 4 is a schematic diagram of a section of an apparatus for the performance of the measurement method according to the invention, with two light sources and one detector.

FIG. 4 shows the details of another measurement array for a process according to the invention, which differs from the embodiments illustrated in FIGS. 2 and 3 in terms of the generation of the measurement and reference light beams M and R, respectively. In the embodiments described in connection with FIGS. 2 and 3, these beams are generated by filtering from two individual beams, which are formed by the optical splitting of an individual light beam from a single light source 20. In the embodiment illustrated in FIG. 4, by contrast, the measurement and reference light beams M and R are generated directly by means of two monochromatic light sources. The example selected involves two power-stabilized laser diodes 80 and 81 with the wavelengths $\lambda_M$ and $\lambda_R$ selected as a function of the material MA to be tested. By using sharply convergent laser light, a very high resolution is achieved, in the range of a few micrometers. An electronic tuning step EA (See FIG. 1) is also possible by controlling the output of the corresponding laser diodes 80 and 81.

The rest of the beam path of the measurement and reference light beams M and R is essentially the same as illustrated in FIG. 3. First, the measurement and reference light beams M and R are conducted, via convergent lenses 82 and 83, respectively, for additional convergence, and are then timed by a chopper 84 so that they alternate with one another in a frequency f3. In addition—for the reasons described above—a second chopper 85 also impresses the frequency f4 on the reference light beam R. Since the laser diodes 80 and 81 which are employed generate very stable output signals, even in alternating operation, the mechanical choppers 84 and 85 can, if so desired, be replaced by an electrical modulation device of a kind well known in the art for providing an electrical modulation having the same effect as caused by the mechanical choppers 84 and 85. For that purpose, all that is necessary is to activate the two laser diodes 80 and 81 in alternating current operation with a phase shift of 180°, so that they are turned on and off in alternation. In order to couple the reference light beam R into the beam path S of the measurement light beam M for an identical measurement point on the material MA to be tested, the reference light beam R is first conducted via a tilted mirror 86 and then via a beam splitter 87. In the illustrated embodiment (e.g., for reasons of drawing space) both beams M and R are shown with their direction rotated by 90° by an additional tilted mirror 88. Once again, there is a convergent lens 89 mounted in front of the material MA to be tested and another convergent lens 90 mounted behind the material MA to be tested. The material MA to be tested can be moved in the directions x and y by a measurement table, shown as 32 in FIG. 3. The detection step DE takes place by means of a single detector 91, which can be identical to the detector 60 shown in FIG. 3.

The remaining structure behind the detector 91 is identical to that illustrated in FIG. 3, and for that reason is not illustrated in any further detail in FIG. 4. Nor is the automatic consideration of the natural intensity difference $I_N$ illustrated here, which can be performed in the manner described above by means of an optical tuning OA, (See FIG. 2), by attenuation of the corresponding light beam ahead of the chopper 84, or an electronic tuning EA, (See FIG. 2), or by means of a power regulation of the corresponding laser diode 80 and/or 81.

Figure 5:
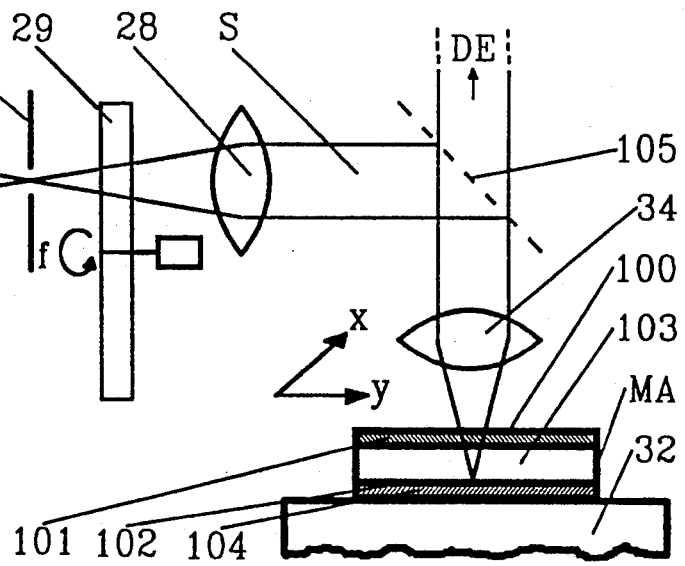
FIG. 5 is a schematic diagram of a section of an apparatus with incident illumination for performance of the process according to the invention.

The embodiment illustrated in FIG. 5 of an arrangement for the performance of a test method according to the invention is substantially the same as the embodiment illustrated in FIG. 2, with the exception that the detection step DE takes place on an incident or directly illuminated side 100 of the material MA to be tested. On account of the similarities between the two arrangements, the details described above are identified by the same reference numbers, letters and symbols as in FIG. 2. Moreover, the arrangement for detection, acquisition, tuning and evaluation is substantially identical to that shown in FIG. 2, and is not explained below in any further detail.

The arrangement illustrated in FIG. 5 can be used if the material MA to be tested does not allow sufficient transmission of the measurement and reference light beams M and R, or if, on account of a specified arrangement of the material MA, there is no room for the transmitted light illumination. FIG. 5 shows an incident illumination arrangement for a solid boyd. This arrangement can also be used, however, to observe the processes of a liquid or gaseous media. It is preferable that the material MA to be tested (in the embodiment selected, the purpose of the measurement is to determine the thickness of an absorbing layer 101 of a solid body) has a reflector 104 provided on its back side 102, which is formed by a transparent substrate 103. In the illustrated example, this involves a metal carrier permanently connected to the transparent substrate 103. However, it can also be a vacuum metallized metal contact (e.g., made of Au) or an external mirror.

The beam path S is conducted to the material MA to be tested by means of a semi-transparent mirror 105. The beam path S is reflected on the reflector 104, then passes through the mirror 105 and is conducted to the detector DE in the manner described above, for example, in connection with FIG. 2. The illumination by the light source 20 and the detection step DE therefore are both carried out on the incident or directly illuminated side 100 of the material MA to be tested, which also saves space.

With this type of arrangement, it is necessary to take into consideration the fact that the measurement light beam M is attenuated twice by the absorbing layer 101, and that the intensity $I_{Rc}$ (See FIG. 1) of the reference light beam R to be detected has two reflection components, by reflection on the surface of the absorbing layer 101 and on the reflector 104. If the reflection component on the surface of the absorbing layer 101 is unknown, it can be removed from the detection DE by an illumination of the material MA using the "dark field" principle, which is well known to those of ordinary skill in the art. The arrangement according to this principle is not explicitly illustrated in FIG. 5, but is well known in the art and described in the Lexicon Der Optik referred to above. It should be briefly noted here that utilization of the "dark field" principle differs from the illustrated arrangement only in details. For example, to block out the component of the light reflected on the surface of the absorbing layer 101, so that it is not erroneously detected for the absorption measurement, the beam path S is deflected by means of a very small tilted mirror (instead of the semi-transparent mirror 105) onto the material MA to be tested. Alternatively, a large tilted mirror with a small hole and an interchange of the light source 20 and detector DE is also possible. The light incidence is perpendicular to the material MA and is focussed on the surface of the absorbing layer 101. Thus, the light component reflected on the surface is returned precisely in the beam path S via the small tilted mirror to the light source 20. It does not get into the detection beam path. The same effect can be achieved if, instead of focusing, parallel light beams strike the material MA to be tested, e.g., by the arrangement of the small tilted mirror between the fourth convergent lens 34 and the material MA to be tested.

The light component which passes through the absorbing and the transparent layers 101 and 103 is reflected on the reflector 104. The latter is opaque, so that the light component is reflected in a large angle. (The same effect is also caused by a rough, scattering back side of the material MA to be tested.) The reflected light is then acquired by the fourth convergent lens 34, which has a correspondingly large aperture, and is conducted past the small tilted mirror into the detection beam path to the detector DE. It is once again necessary to take the repeated absorption of the detected light component into consideration in the evaluation.

Figure 6:
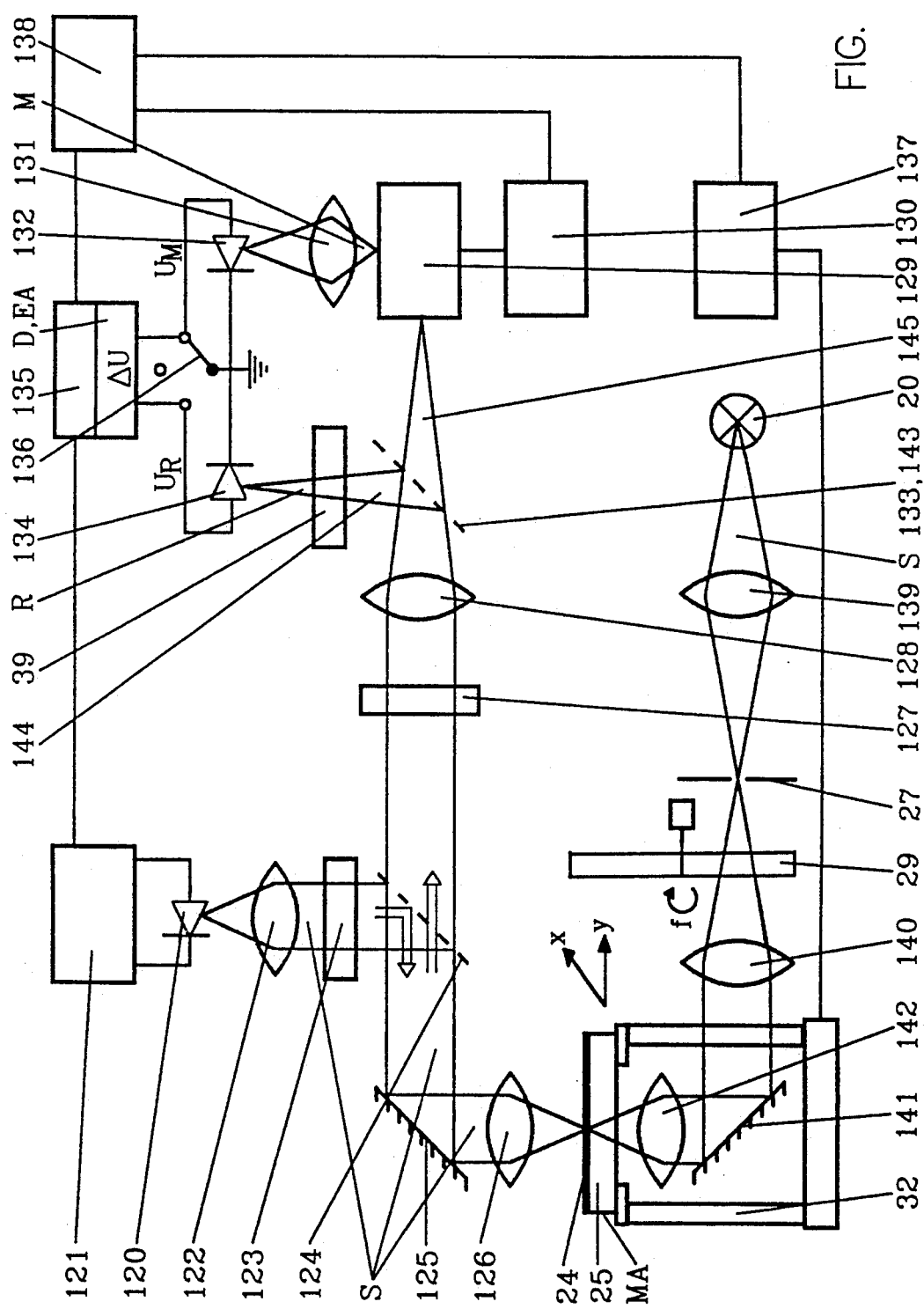
FIG. 6 is a schematic diagram of an apparatus for the performance of the measurement method according to the invention, in combination with the luminescence measurement method.

FIG. 6 illustrates an example of an embodiment for the combination of the measurement method according to the invention for low levels of optical absorption with the luminescence method of the prior art. This method is explained below, schematically, in order to establish the relationship. One important aspect of the invention is the combination of the two methods, which achieves a significant improvement regarding the execution and duration of the method, on account of the calibration of the material MA to be tested, which is necessary only once, and on account of the assignment of the parameters measured by both methods to identical test points. The identification numbers, letters and symbols used in FIG. 2 are also used here, where identical components are involved.

The luminescence method is used to determine characteristic properties of semiconductor materials, in particular the band edge (absorption edge). In technologically important mixed crystals such as InGaAsP or GaAlAs, the band edge can be set by the mixing ratio. The band edge is one of the most important design parameters in opto-electronic components. These parameters can be determined from luminescence emission spectra. For the measurement method for the determination of low levels of optical absorption, it is important that the measurement wavelength is optimally selected from a knowledge of the band edge, and the absorption coefficient of the layer to be tested can be derived from this measurement wavelength. To use the luminescence measurement method, the absorbing layer 24 of the material MA to be tested is illuminated with monochromatic light from a laser diode 120 which is powered by a power supply 121. The beam path S of the light passes through a first convergent lens 122, a color filter 123 to filter out background radiation, a dichroic mirror 124, a tilted mirror 125 and a second convergent lens 126. The material MA is excited by the light so that it emits characteristic radiation (luminescence effect). This luminescence radiation emitted is transmitted via the tilted mirror 125 back to the dichroic mirror 124. The dichroic mirror 124 has the characteristic that it either reflects light or lets it pass as a function of the wavelength of the light in question. It is selected so that the light of the laser diode 120 is reflected, while the light emitted by the material MA is allowed to pass through (as indicated by the arrow s in FIG. 6). After passing through an additional color filter 127 to block out the residual laser radiation, the luminescence radiation is directed by means of a third convergent lens 128 into a monochromator 129. By means of an automatic adjustment 130, the wavelength of the monochromator 129 is varied. Behind the monochromator 129, the spectrally selected light is directed with a fourth convergent lens 131 to a detector 132, where the emission spectrum is detected and recorded.

A second tilted mirror 133 can be placed in the beam path S ahead of the monochromator 129, to measure the integral luminescence (an important indicator of the crystal quality) by means of an additional detector 134. The signals from the detectors 132 and 134 are transmitted to difference inputs of a lock-in amplifier 135, whereby the unnecessary detector 132 or 134 is short-circuited by means of a switch 136. The wavelength adjustment 130 and the measurement table 32, which is moved by means of a stepping motor 137, are controlled by a computer 138. The computer 138 is preferably also used to perform the evaluation.

The measurement method for the determination of low levels of optical absorption LA is now integrated as follows into the apparatus described above for the luminescence measurement. The beam path S emitted by the light source 20 is first conducted as described above via an arrangement of the fifth convergent lens 139, space filter 27, chopper 29 and sixth convergent lens 140, to a third tilted mirror 141. The third tilted mirror 141 deflects the beam path S via a seventh convergent lens 142 onto the material MA to be tested. After the transmission, the beam path S is guided via the second convergent lens 126, the tilted mirror 125, the dichroic mirror 125 (which, in the illustrated example, prevents only the wavelengths of the light from the laser diode 120 from passing through), the color filter 127 and the third convergent lens 128. Instead of the second tilted mirror 133, a beam splitter 143 is now introduced into the beam path. The beam splitter 143 splits the light beam S into a first component beam 144 and a second component beam 145. The reflected first component beam 144 is then filtered through the reference wavelength filter 39 now introduced, so that the reference light beam R is formed. The monochromator 129 is set to the measurement wavelength $\lambda_M$, and the measurement light beam M is filtered out of the second component beam 145. The measurement and reference light beams M and R are then detected simultaneously by the detectors 132 and 134, and the measurement and reference signals $U_M$ and $U_R$ are transmitted to a subtractor D. The switch 136 is thus in a zero position, and does not short circuit either of the two detectors 132 and 134. To obtain the reference signal $U_R$, either the detector 132 can be briefly short-circuited by means of the switch 136, or to achieve a high measurement speed, the reference signal $U_R$ is conducted in parallel to a second lock-in amplifier.

The difference signal $\Delta U$ and reference signal $U_R$, as noted above, are necessary to calculate the layer thickness of the material MA to be tested from the low levels of optical absorption. In the illustrated apparatus for the combined execution of both test methods, the automatic consideration B of the natural intensity difference $\Delta I_N$ necessary for a direct measurement of the low levels of optical absorption is performed by the electronic tuning EA during the subtraction D.

In summary, one feature of the invention resides broadly in the measurement method for the determination of low levels of optical absorption in any desired materials, with an at least quasi-simultaneous detection of the transmission intensities of a measurement light beam and of a reference light beam having different wavelengths, with the measurement light beam being absorbed, and with an analog joint acquisition of the detected measurement and reference signals, taking into consideration the natural intensity difference between the measurement light beam and the reference light beam, characterized by the fact that the low levels of optical absorption are measured directly by the analog joint acquisition of the detected measurement and reference signals in the form of a subtraction with automatic consideration of the natural intensity difference between the measurement and reference light beams by a tuning of the difference formed to zero during a measurement made without the material to be tested.

Another feature of the invention resides broadly in the measurement method, characterized by the fact that the tuning of the difference formed to zero is done optically by attenuating the intensity of the more intense of the two light beams.

Yet another feature of the invention resides broadly in the measurement method, characterized by the fact that the tuning of the difference formed to zero is done electronically by setting a corresponding weighting during the subtraction.

A further feature of the invention resides broadly in the measurement method, characterized by the fact that the measurement and reference light beams are each generated by a monochromatic light source.

A yet further feature of the invention resides broadly in the measurement method, characterized by the fact that the measurement and reference light beams are filtered out of a light beam from a single light source which is optically split after the material transmission.

Yet another further feature of the invention resides broadly in the measurement method, characterized by the fact that the measurement and reference light beams are alternatingly cycled in a first frequency, and the reference light beam is also cycled in a second frequency.

An additional feature of the invention resides broadly in the measurement method, characterized by the fact that the joint light beam is cycled.

A further additional feature of the invention resides broadly in the measurement method, characterized by the fact that the detection of the transmission intensities of the measurement and reference light beams is performed simultaneously.

A yet further additional feature of the invention resides broadly in the measurement method, characterized by the fact that the low levels of optical absorption are measured as a function of a specific measurement point.

Another further additional feature of the invention resides broadly in the measurement method, characterized by the fact that the measurement and reference light beams are focused on the measurement point.

A yet another additional feature of the invention resides broadly in the measurement method, characterized by the fact that, when the material to be tested is a solid body with a rough back side, the focus is on its back side.

Another yet further feature of the invention resides broadly in the measurement method, characterized by the fact that, when the material to be tested has reflecting back side, the detection of the transmission intensities takes place on the illuminated side.

A still further feature of the invention resides broadly in the measurement method, characterized by the fact that the material to be tested is provided with an opaque reflecting back surface and is illuminated according to the dark field principle.

A still further additional feature of the invention resides broadly in the measurement method according to one of the preceding claims, characterized by the fact that it is combined with the luminescence measurement method for the determination of the characteristic properties of the material to be tested.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The invention as described hereinabove in the context of the preferred embodiments is not to be taken as limited to all of the provided details thereof, since modifications and variations thereof may be made without departing from the spirit and scope of the invention.

What is claimed is:

1. A measurement method for determining the optical absorption of a test material having an optical absorption spectrum, said measurement method comprising the steps of:
  a) providing a light source for generating a light beam having a spectrum which includes at least a substantially monochromatic reference light beam (R) at a reference wavelength ($\lambda_R$), said reference wavelength ($\lambda_R$) being selected to be substantially outside of the optical absorption spectrum of the test material, and a substantially monochromatic measurement light beam (M) at a measurement wavelength ($\lambda_M$), said measurement wavelength ($\lambda_M$) being selected to be substantially within the optical absorption spectrum of the test material;
  b) providing detector means for detecting the strength of said reference light beam (R) by generating a reference detector signal ($U_R$) when illuminated by said reference light beam (R) and for detecting the strength of said measurement light beam (M) by generating a measurement detector signal ($U_M$) when illuminated by said measurement light beam (M), each of said reference and measurement detector signals ($U_R$ and $U_M$) generated by said detector means being a signal indicative of the intensity of illumination of said detector means by said reference and measurement light beams (R and M), respectively;
  c) providing difference registration means for registering a difference between said reference detector signal ($U_R$) and said measurement detector signal ($U_M$) generated by said detector means when illuminated by said reference light beam (R) and said measurement light beam (M), respectively;
  d) directly illuminating said detector means with said reference light beam (R) to produce a first reference detector signal ($U_{Ra}$), said direct illumination of said detector means by said reference light beam (R) being carried with the test material absent from the path of said reference light beam (R);
  e) directly illuminating said detector means with said measurement light beam (M) to produce a first measurement detector signal ($U_{Ma}$), said direct illumination of said detector means by said measurement light beam (M) being carried out with the test material absent from the path of said measurement light beam (M);

f) registering a difference ($\Delta = U_{Ra} - U_{Ma}$) between said first reference detector signal ($U_{Ra}$) generated by said detector means when directly illuminated by said inference light beam (R) and a first measurement detector signal ($U_{Ma}$) generated by said detector means when directly illuminated by said measurement light beam (M);

g) providing attenuation means for tuning to zero said difference ($\Delta$) between said first reference detector signal ($U_{Ra}$) and said first measurement detector signal ($U_{Ma}$) by attenuating one of said first reference detector signal ($U_{Ra}$) and said first measurement detector signal ($U_{Ma}$);

h) actuating said attenuation means to thereby balance said first reference detector signal ($U_{Ra}$) and said first measurement detector signal ($U_{Ma}$) to identical values ($U_{Rb} = U_{Mb}$) and thereby tuning to zero said difference ($\Delta$) and maintaining this actuated balanced attenuation status during the following steps:

i) passing said reference light beam (R) through the test material and thereafter illuminating said detector means with said reference light beam (R) to thereby generate a second reference detector signal ($U_{Rc}$);

j) passing said measurement light beam (M) through the test material and thereafter illuminating said detector means with said measurement light beam (M) to thereby generate a second measurement detector signal ($U_{Mc}$); and k) measuring the difference ($\Delta I$) between said second reference signal ($U_{Rc}$) and said second measurement signal ($U_{Mc}$);

whereby said difference ($\Delta I$) is directly indicative of the optical absorption (LA) of the test material; wherein said detector means comprises:

a single detector means provided for detecting alternatively both of said reference light beam (R) and said measurement light beam (M);

wherein said measurement method additionally comprises the further steps of:

modulating both of said reference light beam (R) and said measurement light beam (M) alternatively at a first frequency (f1); and additionally further modulating said reference light beam (R) at a second frequency (f2).

2. The measurement method according to claim 1, wherein said attenuation means is selected from the group consisting of:

optical attenuation means for optically reducing the optical intensity of one of said reference light beam (R) and said measurement light beam (M); and electrical attenuation means for electrically reducing the signal strength of one of said reference detector signal ($U_R$) and said measurement detector signal ($U_M$).

3. The measurement method according to claim 2, wherein said light source comprises polychromatic light generation means for generating polychromatic light having a relatively broad frequency spectrum which includes substantial components at both of said reference wavelength ($\lambda_R$) and said measurement wavelength ($\lambda_M$).

4. The measurement method according to claim 3, wherein said detector means comprises:

splitting means for splitting said light generated by said light generation means into at least two separate light beams;

first filter means for filtering one of said two separate light beams to produce said reference light beam (R), said first filter means comprising means for passing light having a frequency substantially equal to said reference wavelength ($\lambda_R$); and second filter means for filtering the other of said two separate light beams to produce said measurement light beam (M), said second filter means comprising means for passing light having a frequency substantially equal to said measurement wavelength ($\lambda_M$).

5. The measurement method according to claim 4, wherein said step i) of passing said reference light beam (R) through the test material and thereafter illuminating said detector means with said reference light beam (R) to thereby generate second reference detector signal ($U_{Rc}$) and said step j) of passing said measurement light beam (M) through the test material and thereafter illuminating said detector means with said measurement light beam (M) to thereby generate said second measurement detector signal ($U_{Mc}$) are carried out simultaneously.

6. The measurement method according to claim 5, wherein said measurement method additionally comprises the further step of:

modulating, at a frequency (f), said polychromatic light generated by said light polychromatic generation means and having substantial components at both of said reference wavelength ($\lambda_R$) and said measurement wavelength ($\lambda_M$).

7. The measurement method according to claim 6, wherein said measurement method additionally comprises the further step of:

carrying out said step k) with both of said reference light beam (R) and said measurement light beam (M) scanning the test material portion by portion.

8. The measurement method according to claim 7, wherein said measurement method additionally comprises the further step of:

focusing of said reference light beam (R) and of said measurement light beam (M) substantially on the same portion of the test material during the carrying out of said steps a) through k).

9. The measurement method according to claim 8, wherein the test material comprises a solid body having a rough exterior face and wherein the portion of the test material upon which said reference light beam (R) and said measurement light beam (M) are focused lies on said rough exterior face of the test body.

10. The measurement method according to claim 7, wherein behind the test material is provided a reflecting surface, and said detection means is located adjacent to a face of the test material which is opposed to said reflecting surface.

11. The measurement method according to claim 10, wherein behind the test material an opaque reflecting surface is provided, said measurement method additionally comprises the further step of:

illuminating the test material according to the dark field principle.

12. The measurement method according to claim 11, wherein said measurement method additionally comprises the further step of:

carrying out said step k) with both of said reference light beam (R) and said measurement light beam (M) scanning the test material portion by portion.

13. The measurement method according to claim 12, wherein said measurement method additionally comprises the further step of:

focusing of said reference light beam (R) and of said measurement light beam (M) substantially on the same portion of the test material during the carrying out of said steps a) through k).

14. The measurement method according to claim 10, said measurement method additionally comprises the further step of:

carrying out said step k) with both of said reference light beam (R) and said measurement light beam (M) scanning the test material portion by portion.

15. The measurement method according to claim 14, wherein said measurement method additionally comprises the further step of:

focusing of said reference light beam (R) and of said measurement light beam (M) substantially on the same portion of the test material during the carrying out of said steps a) through k).

16. The measurement method according to claim 1, wherein said light source comprises a first substantially monochromatic light generation means for generating a substantially monochromatic light having a wavelength substantially equal to said reference wavelength ($\lambda_R$) and a second substantially monochromatic light generation means for generating a substantially monochromatic light having a wavelength substantially equal to said measurement wavelength ($\lambda_M$).

17. The measurement method according to claim 1, wherein said light source comprises a first substantially monochromatic light generation means for generating a substantially monochromatic light having a wavelength substantially equal to said reference wavelength ($\lambda_R$) and a second substantially monochromatic light generation means for generating a substantially monochromatic light having a wavelength substantially equal to said measurement wavelength ($\lambda_M$); and wherein said attenuation means comprises electrical attenuation means for electrically controlling separately the strengths of the light beams (R and M) of said first and said second light sources generating substantially monochromatic light beams at said wavelengths ($\lambda_R$ and $\lambda_M$), respectively.

18. The measurement method according to claim 17, wherein said detector means comprises:

a single detector means provided for detecting alternatively both of said reference light beam (R) and said measurement light beam (M);

wherein said measurement method additionally comprises the further steps of:

modulating both of said reference light beam (R) and said measurement light beam (M) alternatively at a first frequency (f1); and additionally further modulating said reference light beam (R) at a second frequency (f2).

19. The measurement method according to claim 18, wherein said measurement method additionally comprises the further step of:

carrying out said step k) with both of said reference light beam (R) and said measurement light beam (M) scanning the test material portion by portion.

20. The measurement method according to claim 19, wherein said measurement method additionally comprises the further step of:

focusing of said reference light beam (R) and of said measurement light beam (M) substantially on the same portion of the test material during the carrying out of said steps a) through k).

21. The measurement method according to claim 20, wherein the test material comprises a solid body having a rough exterior face and wherein the portion of the test material upon which said reference light beam (R) and said measurement light beam (M) are focused lies on said rough exterior face of the test body.

22. The measurement method according to claim 18, wherein behind the test material is provided a reflecting surface, and said detection means is located adjacent to a face of the test material which is opposed to said reflecting surface.

23. The measurement method according to claim 22, wherein behind the test material an opaque reflecting surface is provided, said measurement method additionally comprises the further step of:

illuminating the test material according to the dark field principle.

24. The measurement method according to claim 23, wherein said measurement method additionally comprises the further step of:

carrying out said step k) with both of said reference light beam (R) and said measurement light beam (M) scanning the test material portion by portion.

25. The measurement method according to claim 24, wherein said measurement method additionally comprises the further step of:

focusing of said reference light beam (R) and of said measurement light beam (M) substantially on the same portion of the test material during the carrying out of said steps a) through k).

26. The measurement method according to claim 22, wherein said measurement method additionally comprises the further step of:

carrying out said step k) with both of said reference light beam (R) and said measurement light beam (M) scanning the test material portion by portion.

27. The measurement method according to claim 26, wherein said measurement method additionally comprises the further step of:

focusing of said reference light beam (R) and of said measurement light beam (M) substantially on the same portion of the test material during the carrying out of said steps a) through k).

28. The measurement method according to claim 1, wherein said measurement method additionally comprises the further step of:

exciting the test material such that the test material emits a characteristic radiation associated with the luminescence effect of the test material.

29. The measurement method according to claim 1, wherein said attenuation means comprises at least one of:

optical attenuation means for optically reducing the optical intensity of one of said reference light beam (R) and said measurement light beam (M); and electrical attenuation means for electrically reducing the signal strength of one of said reference detector signal ($U_R$) and said measurement detector signal ($U_M$); and said light source comprises polychromatic light generation means for generating polychromatic light having a relatively broad frequency spectrum which includes substantial components at both of said reference wavelength ($\lambda_R$) and said measurement wavelength ($\lambda_M$);

wherein said detector means comprises:

splitting means for splitting said light generated by said light generation means into at least two separate light beams;

first filter means for filtering one of said two separate light beams to produce said reference light beam (R), said first filter means comprising means for passing light having a frequency substantially equal to said reference wavelength ($\lambda_R$); and second filter means for filtering the other of said two separate light beams to produce said measurement light beam (M), said second filter means comprising means for passing light having a frequency substantially equal to said measurement wavelength ($\lambda_M$); wherein said step i) of passing said reference light beam (R) through the test material and thereafter illuminating said detector means with said reference light beam (R) to thereby generate second reference detector signal ($U_{Rc}$) and said step j) of passing said measurement light beam (M) through the test material and thereafter illuminating said detector means with said measurement light beam (M) to thereby generate said second measurement detector signal ($U_{Mc}$) are carried out simultaneously;

wherein said measurement method additionally comprises the further step of:

modulating, at a frequency (f), said polychromatic light generated by said light polychromatic generation means and having substantial components at both of said reference wavelength ($\lambda_R$) and said measurement wavelength ($\lambda_M$); and wherein behind the test material is provided a reflecting surface, and said detection means is located adjacent to a face of the test material which is opposed to said reflecting surface;

wherein behind the test material an opaque reflecting surface is provided, said measurement method additionally comprises the further step of:

illuminating the test material according to the dark field principle; wherein said measurement method additionally comprises the further steps of:

carrying out said step k) with both of said reference light beam (R) and said measurement light beam (M) scanning the test material portion by portion; and focusing of said reference light beam (R) and of said measurement light beam (M) substantially on the same portion of the test material during the carrying out of said steps a) through k).

30. A measurement method for determining the optical absorption of a semiconductor layer or a semiconductor wafer having an optical absorption spectrum, said measurement method comprising the steps of:

a) providing a light source for generating a light beam having a spectrum which includes at least a substantially monochromatic reference light beam (R) at a reference wavelength ($\lambda_R$), said reference wavelength ($\lambda_R$) being selected to be substantially outside of the optical absorption spectrum of the semiconductor layer or semi-conductor wafer to be tested, and a substantially monochromatic measurement light beam (M) at a measurement wavelength ($\lambda_M$), said measurement wavelength ($\lambda_M$) being selected to be substantially within the optical absorption spectrum of the semiconductor layer or semiconductor wafer to be tested;

b) providing detector means for detecting the strength of said reference light beam (R) by generating a reference detector signal ($U_R$) when illuminated by said reference light beam (R) and for detecting the strength of said measurement light beam (M) by generating a measurement detector signal ($U_M$) when illuminated by said measurement light beam (M), each of said reference and measurement detector signals ($U_R$ and $U_M$) generated by said detector means being a signal indicative of the intensity of illumination of said detector means by said reference and measurement light beams (R and M), respectively;

c) providing difference registration means for registering a difference between said reference detector signal ($U_R$) and said measurement detector signal ($U_M$) generated by said detector means when illuminated by said reference light beam (R) and said measurement light beam (M), respectively;

d) directly illuminating said detector means with said reference light beam (R) to produce a first reference detector signal ($U_{Ra}$), said direct illumination of said detector means by said reference light beam (R) being carried with the semiconductor layer or semi-conductor wafer absent from the path of said reference light beam (R);

e) directly illuminating said detector means with said measurement light beam (M) to produce a first measurement detector signal ($U_{Ma}$), said direct illumination of said detector means by said measurement light beam (M) being carried out with the semiconductor layer or semiconductor wafer absent from the path of said measurement light beam (M);

f) registering a difference ($\Delta = U_{Ra} - U_{Ma}$) between said first reference detector signal ($U_{Ra}$) generated by said detector means when directly illuminated by said inference light beam (R) and a first measurement detector signal ($U_{Ma}$) generated by said detector means when directly illuminated by said measurement light beam (M);

g) providing attenuation means for tuning to zero said difference ($\Delta$) between said first reference detector signal ($U_{Ra}$) and said first measurement detector signal ($U_{Ma}$) by attenuating one of said first reference detector signal ($U_{Ra}$) and said first measurement detector signal ($U_{Ma}$);

h) actuating said attenuation means to thereby balance said first reference detector signal ($U_{Ra}$) and said first measurement detector signal ($U_{Ma}$) to identical values ($U_{Rb} = U_{Mb}$) and thereby tuning to zero said difference ($\Delta$) and maintaining this actuated balanced attenuation status during the following steps:

i) passing said reference light beam (R) through the semi-conductor layer or semiconductor wafer and thereafter illuminating said detector means with said reference light beam (R) to thereby generate a second reference detector signal ($U_{Rc}$);

j) passing said measurement light beam (M) through the semi-conductor layer or semiconductor wafer and thereafter illuminating said detector means with said measurement light beam (M) to thereby generate a second measurement detector signal ($U_{Mc}$); and k) measuring the difference ($\Delta I$) between said second reference signal ($U_{Rc}$) and said second measurement signal ($U_{Mc}$);

whereby said difference (ΔI) is directly indicative of the optical absorption (LA) of the semiconductor layer or semiconductor wafer;
wherein said detector means comprises:
a single detector means provided for detecting alternatively both of said reference light beam (R) and said measurement light beam (M);
wherein said measurement method additionally comprises the further steps of:
modulating both of said reference light beam (R) and said measurement light beam (M) alternatively at a first frequency (f1); and
additionally further modulating said reference light beam (R) at a second frequency (f2).

31. A measurement method for determining the optical absorption of a test material having an optical absorption spectrum, said measurement method comprising the steps of:

a) providing a light source for generating a light beam having a spectrum which includes at least a substantially monochromatic reference light beam (R) at a reference wavelength ($\lambda_R$), said reference wavelength ($\lambda_R$) being selected to be substantially outside of the optical absorption spectrum of the test material, and a substantially monochromatic measurement light beam (M) at a measurement wavelength ($\lambda_M$), said measurement wavelength ($\lambda_M$) being selected to be substantially within the optical absorption spectrum of the test material;

b) providing detector means for detecting the strength of said reference light beam (R) by generating a reference detector signal ($U_R$) when illuminated by said reference light beam (R) and for detecting the strength of said measurement light beam (M) by generating a measurement detector signal ($U_M$) when illuminated by said measurement light beam (M), each of said referece and measurement detector signals ($U_R$ and $U_M$) generated by said detector means being a signal indicative of the intensity of illumination of said detector means by said reference and measurement light beams (R and M), respectively;

c) providing difference registration means for registering a difference between said reference detector signal ($U_R$) and said measurement detector signal ($U_M$) generated by said detector means when illuminated by said reference light beam (R) and said measurement light beam (M), respectively;

d) directly illuminating said detector means with said reference light beam (R) to produce a first reference detector signal ($U_{Ra}$), said direct illumination of said detector means by said reference light beam (R) being carried out with the test material absent from the path of said reference light beam (R);

e) directly illuminating said detector means with said measurement light beam (M) to produce a first measurement detector signal ($U_{Ma}$), said direct illumination of said detector means by said measurement light beam (M) being carried out with the test material absent from the path of said measurement light beam (M);

f) registering a difference ($\Delta = U_{Ra} - U_{Ma}$) between said first reference detector signal ($U_{Ra}$) generated by said detector means when directly illuminated by said inference light beam (R) and a first measurement detector signal ($U_{Ma}$) generated by said detector means when directly illuminated by said measurement light beam (M);

g) providing attenuation means for tuning to zero said difference (Δ) between said first reference detector signal ($U_{Ra}$) and said first measurement detector signal ($U_{Ma}$) by attenuating one of said first reference detector signal ($U_{Ra}$) and said first measurement detector signal ($U_{Ma}$);

h) actuating said attenuation means to thereby balance said first reference detector signal ($U_{Ra}$) and said first measurement detector signal ($U_{Ma}$) to identical values ($U_{Rb} = U_{Mb}$) and thereby tuning to zero said difference (Δ) and maintaining this actuated balanced attenuation status during the following steps:

i) passing said reference light beam (R) through the test material and thereafter illuminating said detector means with said reference light beam (R) to thereby generate a second reference detector signal ($U_{Rc}$);

j) passing said measurement light beam (M) through the test material and thereafter illuminating said detector means with said measurement light beam (M) to thereby generate a second measurement detector signal ($U_{Mc}$);

k) measuring the difference (ΔI) between said second reference signal ($U_{Rc}$) and said second measurement signal ($U_{Mc}$);

whereby said difference (ΔI) is directly indicative of the optical absorption (LA) of the test material;
wherein said attenuation means is selected from the group consisting of:
optical attenuation means for optically reducing the optical intensity of one of said reference light beam (R) and said measurement light beam (M); and
electrical attenuation means for electrically reducing the signal strength of one of said reference detector signal ($U_R$) and said measurement detector signal ($U_M$);
wherein said light source comprises polychromatic light generation means for generating polychromatic light having a relatively broad frequency spectrum which includes substantial components at both of said reference wavelength ($\lambda_R$) and said measurement wavelength ($\lambda_M$);
wherein said detector means comprises:
a single detector means provided for detecting alternatively both of said reference light beam (R) and said measurement light beam (M);
wherein said measurement method additionally comprises the further steps of:
modulating both of said reference light beam (R) and said measurement light beam (M) alternatively at a first frequency (f1); and
additionally further modulating said reference light beam (R) at a second frequency (f2).

32. The measurement method according to claim 31, wherein said measurement method additionally comprises the further step of:
carrying out said step k) with both of said reference light beam (R) and said measurement light beam (M) scanning the test material portion by portion.

33. The measurement method according to claim 32, wherein said measurement method additionally comprises the further step of:
focusing of said reference light beam (R) and of said measurement light beam (M) substantially on the same portion of the test material during the carrying out of said steps a) through k).

34. The measurement method according to claim 33, wherein the test material comprises a solid body having a rough exterior face and wherein the portion of the test material upon which said reference light beam (R) and said measurement light beam (M) are focused lies on said rough exterior face of the test body.

35. The measurement method according to claim 31, wherein behind the test material is provided a reflecting surface, and said detection means is located adjacent to a face of the test material which is opposed to said reflecting surface.

36. The measurement method according to claim 35, wherein behind the test material an opaque reflecting surface is provided, said measurement method additionally comprises the further step of:

illuminating the test material according to the dark field principle.

37. The measurement method according to claim 36, wherein said measurement method additionally comprises the further step of:

carrying out said step k) with both of said reference light beam (R) and said measurement light beam (M) scanning the test material portion by portion.

38. The measurement method according to claim 37, wherein said measurement method additionally comprises the further step of:

focusing of said reference light beam (R) and of said measurement light beam (M) substantially on the same portion of the test material during the carrying out of said steps a) through k).

39. The measurement method according to claim 35, wherein said measurement method additionally comprises the further step of:

carrying out said step k) with both of said reference light beam (R) and said measurement light beam (M) scanning the test material portion by portion.

40. The measurement method according to claim 39, wherein said measurement method additionally comprises the further step of:

focusing of said reference light beam (R) and of said measurement light beam (M) substantially on the same portion of the test material during the carrying out of said steps a) through k).

* * * * *